US008071298B2

(12) United States Patent
Abbas et al.

(10) Patent No.: US 8,071,298 B2
(45) Date of Patent: Dec. 6, 2011

(54) INCREASED ETHANOL PRODUCTION FROM XYLOSE

(75) Inventors: Charles Abbas, Champaign, IL (US); Andriy A. Sibirny, Lviv (UA); Andriy Y. Voronovsky, Lviv (UA); Oleh V. Stasyk, Lviv (UA); Olena P. Ishchuk, Lviv (UA); Olena B. Ryabova, Lviv (UA)

(73) Assignee: Archer Daniels Midland Company, Decatur, IL (US)

( * ) Notice: Subject to any disclaimer, the term of this patent is extended or adjusted under 35 U.S.C. 154(b) by 416 days.

(21) Appl. No.: 12/103,861

(22) Filed: Apr. 16, 2008

(65) Prior Publication Data

US 2008/0254524 A1 Oct. 16, 2008

Related U.S. Application Data

(60) Provisional application No. 60/923,605, filed on Apr. 16, 2007.

(51) Int. Cl.
*C12Q 1/68* (2006.01)
*C12N 15/11* (2006.01)
*C12N 1/19* (2006.01)

(52) U.S. Cl. ............. 435/6.1; 536/23.1; 435/254.2

(58) Field of Classification Search .................. None
See application file for complete search history.

(56) References Cited

U.S. PATENT DOCUMENTS

| | | | |
|---|---|---|---|
| 4,368,268 A | 1/1983 | Gong | |
| 5,554,520 A * | 9/1996 | Fowler et al. | 435/165 |
| 5,935,789 A * | 8/1999 | Rhee et al. | 435/6 |
| 6,258,559 B1 | 7/2001 | Zamost | |
| 6,582,944 B1 | 6/2003 | Hallborn et al. | |
| 2003/0082815 A1 | 5/2003 | Abbas et al. | |
| 2004/0142456 A1 | 7/2004 | Jeffries et al. | |
| 2004/0231661 A1 | 11/2004 | Griffin et al. | |
| 2005/0153411 A1 | 7/2005 | Wahlbom et al. | |
| 2006/0075522 A1 | 4/2006 | Cleveland et al. | |
| 2006/0110810 A1 | 5/2006 | Rajgarhia et al. | |

OTHER PUBLICATIONS

GenBank accession No. Q12629.*
Ryabova et al., "Xylose and Cellobiose Fermentation to Ethanol by the Thermotolerant Methylotrophic Yeast Hansenula Polymorpha", FEMS Yeast Research 4 (2003) 157-164.
Voronovsky et al., "Expression of xylA Genes encoding Xylose Isomerases from *Escherichia coli* and *Streptomyces coelicolor* in the Metholotrophic Yeast Hansenula Polymorpha", FEMS Yeast Res. Nov. 5, 2005;(11):1055-62, Epub Oct. 10, 2005, PMID: 16243589 [PubMed—indexed for MEDLINE].

Voronovsky et al., "Expression of xylA Genes encoding Xylose Isomerases from *Escherichia coli* and *Streptomyces coelicolor* in the Metholotrophic Yeast Hansenula Polymorpha", FEMS Yeast Res. Nov. 5, 2005(11):1055-62.
Toivari et al., "Conversion of Xylose to Ethanol by Recombinant *Saccharomyces cerevisiae*: Importance of Xylulokinase (XKS1) and Oxygen Availability", Metabolic Engineering 3, 236-249 (2001).
Ryabova et al., "Xylose and Cellobiose Fermentation to Ethanol by the Thermotolerant Methylotrophic Yeast Hansenula Polymorpha", FEMS Yeast Res. Nov. 4, 2003(2):157-64, PMID: 14613880 [PubMed—indexed for Medline].
Sybirna, K. et al., "A New Hansenula Polymorpha HAP4 Homologue which Contains only the N-Terminal Conserved Domain of the Protein is Fully Functional in *Saccharomyces cerevisiae*", Current Genetics, vol. 47, No. 3, Mar. 2005 (SpringerLink.com).
Jin et al., "*Saccharomyces cerevisiae* Engineered for Xylose Metabolism Exhibits a Respiratory Response", Applied and Environmental Microbiology, vol. 70, No. 11, Nov. 2004, p. 6816-6825.
Porro et al., "Replacement of a Metabolic Pathway for Large-Scale Production of Lactic Acid from Engineered Yeasts", Applied and Environmental Microbiology, vol. 65, No. 9, Sep. 1999, p. 4211-4215.
Hoek et al., "Effects of Pyruvate Decarboxylase Overproduction on Flux Distribution at the Pyruvate Branch Point in Saccharomyces cerevisiae", Applied and Environmental Microbiology, vol. 64, No. 6, Jun. 1998, p. 2133-2140.
Pitkanen, "Impact of Xylose and Mannose on Central Metabolism of Yeast *Saccharomyces cerevisiae*", Helsinki University of Technology, Dept. of Chemical Technology, Technical Biochemistry Report Jan. 2005, Espoo 2005.
Hoek et al., "Effects of Pyruvate Decarboxylase Overproduction on Flux Distribution at the Pyruvate Branch Point in *Saccharomyces cerevisiae*", Applied and Environmental microbiology, vol. 64, No. 6, Jun. 1998, p. 2133-2140.
Jeffries et al., "Metabolic Engineering for Improved Fermentation of Pentoses by Yeasts", Appl. Microbiol Biotechnol (2004) 63: 495-509.
Jin et al., "Stoichiometric Network Constraints on Xylose Metabolism by Recombinant *Saccharomyces cerevisiae*", Metabolic Engineering 6, (2004) 229-238.
International Search Report dated Oct. 20, 2008.
Souciet et al., "Genomic Exploration of the Hemiascomycetous Yeasts: 1. A Set of Yeast Species for Molecular Evolution Studies", FEBS Letters, 2000, vol. 487, pp. 3-12.
Dujon et al., "Genome Evolution in Yeasts", Nature, Jul. 1, 2004, vol. 430, pp. 35-44.
GENBANK Assession No. AAL433546, Jul. 8, 2001.

* cited by examiner

*Primary Examiner* — Michele K Joike

(74) *Attorney, Agent, or Firm* — Mark W. Roberts

(57) ABSTRACT

Methods and compositions for the production of ethanol from lignocellulosic starting materials are provided herein. Embodiments of the invention provide methods of manipulating the carbon flux of a host cell transformed with plasmids of the invention. Plasmids of the invention may include nucleotides that encode pyruvate decarboxylase. In one embodiment, a strain of the thermotolerant yeast *Hansenula polymorpha* that has been transformed with plasmids and polynucleotides of the invention is provided.

22 Claims, 24 Drawing Sheets

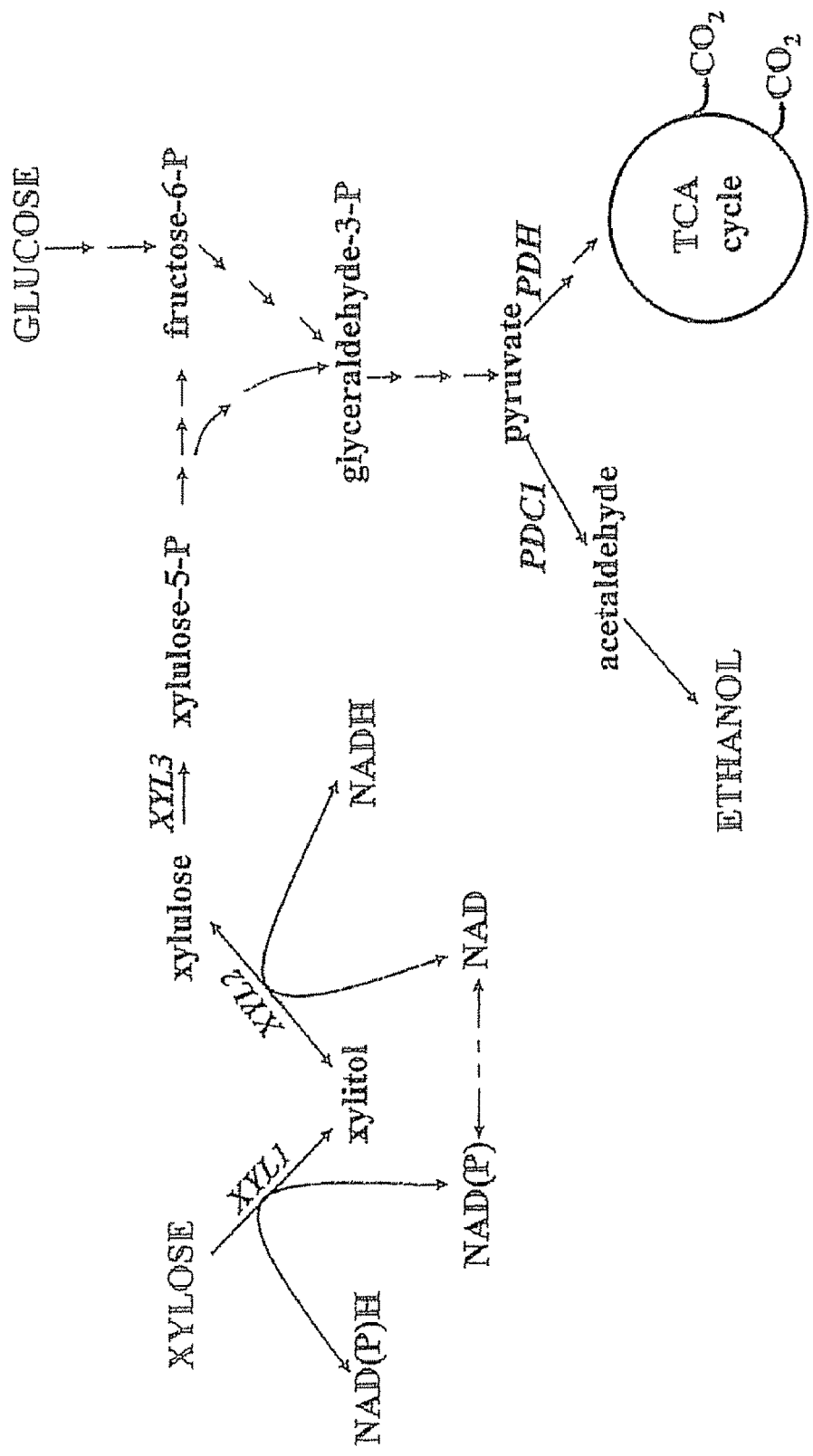
Fig. 1. Scheme of xylose and glucose metabolism in yeasts

>HpPDC1
ATGTCTGAATCCCAACTACCTTCTAAAATTCCCTTTGGCCGCTACGTGTTTGAGCGTATCAAGCAAGTCGGAGT
GAACACCATTTTCGGTGTTCCTGGTGACTTCAACCTGTCTCTGCTGGACCACATCTACACTGTGGACGGCCTGA
GATGGGCCGGTAACGCCAACGAGCTCAATGCGGGCTATTCTGCGGACGGTTACTCCCGTATCAACGGCATGTCC
TGTCTGGTGACCACCTTTGGTGTCGGCGACTTATCGGCAGTCAATGCCATTGCGGGCATGATGGCCGAGCACGT
TGGATGTCTGCACATTGTCGGCACGCCTTCGCTCTCCAGTATCTCGAACAGACTGCTGCTGCACCACACACTGG
GTAACGGCCGGTTCGACATTTTCGAGGAGATGTCCAAGCACATCACCCAGAAGACCTCCAGCATCGACGATATT
AGAACGGCACAGGCTGTTCTGGACGACCTGATCGAGACCGCATACACCACCAAGAGACCGGTGTATTTGGGACT
GCCTTCGAACTTTGTGGACCAGCTGGTCGACTCCGAGCGGCTCAAGACGCCATTGAAGCTGACCCTTCCTCCAA
ACGACAAGCTTGCCGAGGACGAGATTGTCGAGAGCATCTTCAACAAGATTGTCGAGGCCAAGGACCCAATTATG
CTGGTGGATGCCTGCGCTTCGAGACACGATGTGCAGGACCTTGTGGCGCAATTCGTCGAGGCCACGAAATTCCC
CGTCTACACCACGCCTATGGGCAAGTCGGCCTTCAGCGAGGACCATTCCAGATTTGGCGGTGTGTACATCGGAG
TTCTGTCGAACCCGGACGTGAAGGAGGCGGTCGAGTCGTCCGACTTGATCCTCAGCGTCGGCGGCCTGCTGTCG
GACTTCAACACGGGCTCGTTCTCGTACAACTACCACACCACCAACGTGATCGAGTTCCACTCCGACTTCTGTAA
AGTGCGTGCTGCCACGTACGCAGACGTCAAGATGAAGTACGTCTTGGAGAGACTGTGCCGCAAGATCAAGGAGG
CCAAACTGGACTACGTGCCACAGCCGCTGCCGGAGTCCGTCCAGGACTACAAGAAGGTGGCCAATATCAAGTCT
GGCAAGCTGACTCAGGACTACTTGTGGAAAAAACTCTCCTTTTTCCTGCGCTCTGGCGACGTTCTGGTCACCGA
GACAGGCACGTCTTCGTTCGGTGTGACCCAGACGCATTTCCCAGGCAACATCACGGCTATTTCCCAGGTTCTGT
GGGGCTCGATCGGTTATTCGCTTCCTTCTGCCACCGGCGCGCAATTCGCGCTCGAGGAGATCGATCCTAACCGC
AGATGTATTCTGTTCATTGGTGACGGCTCTTTGCAGCTGACCGTCCAGTCCATCTCGGATATCTGCCGCTGGAA
TCTCAAGCCATATCTCTTTGTGCTCAACAACAACGGTTACGATCGAGAAGCTGATTCACGGCCTAAGGCAC
AGTACAACATGATCCAGAAATGGGATCACTTCAAGATTCTCGAGCTGTTCCATGACAAAGTCGACTACGAGAAC
CACCGCGTGTCGACGATCGAGGAGCTGAACGCTCTGTTTGCCGACGAGGCCTTTAACAAAAACGACAAGGTCAG
ACTGATCGAGATCATGCTCGACGAGATGGACGCACCGGAGAACCTTGTCAAGCAAGCCAAGATCTCGGAGCAGA
TCAATGCAGCTTAA (SEQ ID NO:3)

Figure 2. Sequence of the *Hansenula polymorpha* PDC1 ORF.

>KlPDC1
ATGTCTGAAATTACATTAGGTCGTTACTTGTTCGAAAGATTAAAGCAAGTCGAAGTTCAAACCATCTTTGGTCT
ACCAGGTGATTTCAACTTGTCCCTATTGGACAATATCTACGAAGTCCCAGGTATGAGATGGGCTGGTAATGCCA
ACGAATTGAACGCTGCTTACGCTGCTGATGGTTACGCCAGATTAAAGGGTATGTCCTGTATCATCACCACCTTC
GGTGTCGGTGAATTGTCTGCTTTGAACGGTATTGCCGGTTCTTACGCTGAACACGTTGGTGTCTTGCACGTTGT
CGGTGTTCCATCCGTCTCTTCTCAAGCTAAGCAATTGTTGTTGCACCACACCTTGGGTAACGGTGACTTCACTG
TTTTCCACAGAATGTCCTCCAACATTTCTGAAACCACTGCTATGATCACCGATATCAACACTGCCCCAGCTGAA
ATCGACAGATGTATCAGAACCACTTACGTTTCCCAAAGACCAGTCTACTTGGGTTTGCCAGCTAACTTGGTCGA
CTTGACTGTCCCAGCTTCTTTGTTGGACACTCCAATTGATTTGAGCTTGAAGCCAAATGACCCAGAAGCCGAAG
AAGAAGTCATCGAAAACGTCTTGCAACTGATCAAGGAAGCTAAGAACCCAGTTATCTTGGCTGATGCTTGTTGT
TCCAGACACGATGCCAAGGCTGAGACCAAGAAGTTGATCGACTTGACTCAATTCCCAGCCTTCGTTACCCCAAT
GGGTAAGGGTTCCATTGACGAAAAGCACCCAAGATTCGGTGGTGTCTACGTCGGTACCCTATCTTCTCCAGCTG
TCAAGGAAGCCGTTGAATCTGCTGACTTGGTTCTATCGGTCGGTGCTCTATTGTCCGATTTCAACACTGGTTCT
TTCTCTTACTCTTACAAGACCAAGAACATTGTCGAATTCCACTCTGACTACACCAAGATCAGAAGCGCTACCTT
CCCAGGTGTCCAAATGAAGTTCGCTTTACAAAAATTGTTGACTAAGGTTGCCGATGCTGCTAAGGGTTACAAGC
CAGTTCCAGTTCCATCTGAACCAGAACACAACGAAGCTGTCGCTGACTCCACTCCATTGAAGCAAGAATGGGTC
TGGACTCAAGTCGGTGAATTCTTGAGAGAAGGTGATGTTGTTATCACTGAAACCGGTACCTCTGCCTTCGGTAT
CAACCAAACTCATTTCCCAAACAACACATACGGTATCTCTCAAGTTTTATGGGGTTCCATTGGTTTCACCACTG
GTGCTACCTTGGGTGCTGCCTTCGCTGCCGAAGAAATTGATCCAAAGAAGAGAGTTATCTTATTCATTGGTGAC
GGTTCTTTGCAATTGACTGTTCAAGAAATCTCCACCATGATCAGATGGGGCTTGAAGCCATACTTGTTCGTATT
GAACAACGACGGTTACACCATTGAAAGATTGATTCACGGTGAAACCGCTCAATACAACTGTATCCAAAACTGGC
AACACTTGGAATTATTGCCAACTTTCGGTGCCAAGGACTACGAAGCTGTCAGAGTTTCCACCACTGGTGAATGG
AACAAGTTGACCACTGACGAAAAGTTCCAAGACAACACCAGAATCAGATTGATCGAAGTTATGTTGCCAACTAT
GGATGCTCCATCTAACTTGGTTAAGCAAGCTCAATTGACTGCTGCTACCAACGCTAAGAACTAA (SEQ ID NO:4)

Figure 3. Sequence of the *Kluyveromyces lactis* PDC1 ORF.

>HpGAP promoter
CAATTATCATTAATAATCACTCATGATCCCTGCGTCTAGAGGTTGGTCTAGACCACATCCGTGCACCAGACAAG
ACACGGCCCACGGAGGTAAAGGTGCCAACTCGCAAAGTGCAACAACCATGGCTCTCCAGCACGGTGCGTGGGGT
AAAGACAATCTCCGGGAACCGATCCCGAAACCGAGAAAGAGGGTTTTAAGCGTGTGTCCTTTGCGGAGGCGGTG
TAGCACTTCTTATTGTCCTTTGGGCCGCTCCGGCGGTTGAGCTTCCACAGAACATCCTTGCACGGACAAGCAGT
CCCGGAGACGCCATGTTGGGTGATACCCACTTCTGGCTGTACAGAGCTTTATATCACCTTACCTGGCGCTAGAG
TAGACCCAATTCCCGACTCACACCACCCTCACATGCAGAACTAACCAATAAGGTAATTAATTAACACGATATAG
CTCGTGGTGAACACTGGCCCGGAGTAGTCATACGTGTAGGTTTTTGGCGTGATGAAAATCAGGTGGAGCACGAC
TTTTCGTAATGTTCGGGAGGGAGTGCTGCAAACGGTATATAAGGACCAGTTTTTCTCGCAACATTATCAATTGC
TCTTTAGTACAAAGATAATATAGAAACAAAATG (SEQ ID NO:5)

Figure 4. The promoter sequence of the *H polymorpha* glyceraldehyde 3-phosphate dehydrogenase gene (*HpGAP*) Start codon of the gene is written with red.

```
>HpAOX terminator
AAGCTTGGAGACGTGGAAGGACATACCGCTTTTGAGAAGCGTGTTTGAAAATAGTTCTT
TTTCTGGTTTATATCGTTTATGAAGTGATGAGATGAAAAGCTGAAATAGCGAGTATAGG
AAAATTTAATGAAAATTAAATTAAATATTTTCTTAGGCTATTAGTCACCTTCAAAATGC
CGGCCGCTTCTAAGAACGTTGTCATGATCGACAACTACGACTCGTTACCTGGAACCTG
TACGAGTACCTGTGTCAGGAGGGAGCCAATGTCGAGGTTTTCAGGAACGATCAGATCAC
CATTCCGGAGATTGAGCAGCTCAAGCCGGACGTTGTGGTGATATCCCCTGGTCCTGGCC
ATCCAAGAACAGACTCGGGAATATCTCGCGACGTGATCAGCCATTTTAAAGGCAAGATT
CCTGTCTTTGGTGTCTGTATGGGCCAGCAGTGTATCTTCGAGGAGTTTGGCGGAGACGT
CGAGTATGCGGGCGAGATTGTCCATGGAAAAACGTCCACTGTTAAGCACGACAACAAGG
GAATGTTCAAAAACGTTCCGCAAGATGTTGCTGTCACCAGATACCACTCGCTGGCCGGA
ACGCTCAAGTCGCTTCCGGACTGTCTAGAGATCACTGCTCGCACAGACAACGGGATCAT
TATGGGTGTGAGACACAAGAAGTACACCATCGAGGGCGTCCAGTTTCATCCAGAGAGCA
TTCTGACCGAGGAGGGCCATCTGATGATCCAGAATATCCTCAACGTTTCCGGTGGTTAC
TGGGAGGAAAATGCCAACGGCGCGGCTCAGAGAAAGGAAAGCATATTGGAGAAAATATA
CGCGCAGAGACGAAAAGACTACGAGTTTGAGATGAACAGACCGGGGCGCAGATTTGCTG
ATCTAGAACTGTACTTGTCCATGGGACTGGCACCGCCGCTAATCAATTTTTACGACAGA
TTGGAGCAGAACATCAGCGCCGGCAAGGTTGCAATTCTCAGCGAAATCAAGAGAGCGTC
GCCTTCTAAAGGCGTCATCGACGGAGACGCTAACGCTGCCAAACAGGCCCTCAACTACG
CCAAGGCTGGAGTTGCCACAATTTCTGTTTTGACCGAGCCAACCTGGTTTAAAGGAAAT
ATCCAGGACCTGGAGGTGGCCAGAAAAGCCATTGACTCTGTGGCCAATAGACCGTGTAT
TTTGCGGAAGGAGTTTATCTTCAACAAGTACCAAATTCTAGAGGCCCGACTGGCGGGAG
CAGACACGGTTCTGCTGATTGTCAAGATGCTGAGCTC (SEQ ID NO:6)
```

Figure 5. Terminator sequence of the *H. polymorpha* alcohol oxidase gene (*HpAOX*).

Figure 7. Scheme of the plasmid pKlPDC1 containing the ORF of the Kluyveromyces lactis PDC1 gene driven by the HpGAP promoter ($P_{GAP}$).

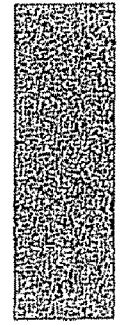
Figure 14

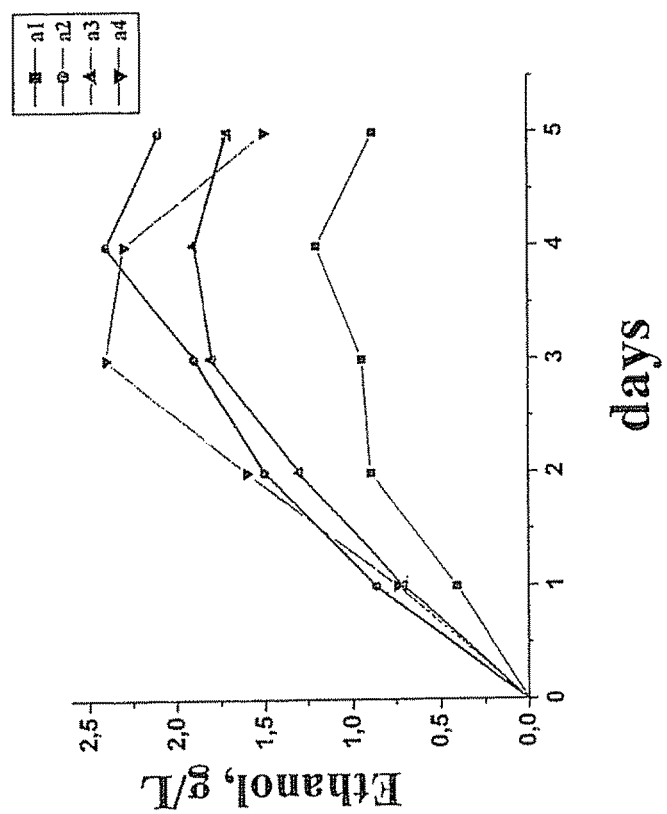
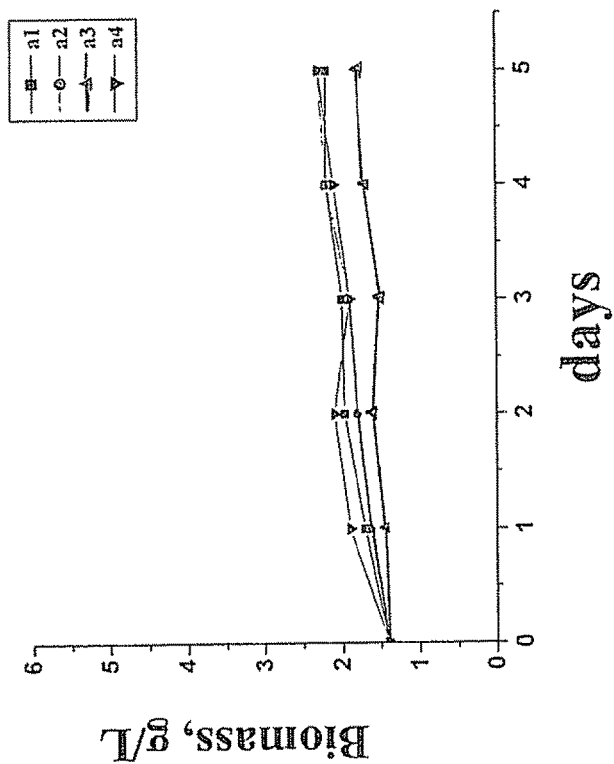
Figure 17

SEQUENCE LISTING

<160> NUMBER OF SEQ ID NOS: 14

<210> SEQ ID NO 1
<211> LENGTH: 571
<212> TYPE: PRT
<213> ORGANISM: Hansenula polymorpha

<400> SEQUENCE: 1

Met Ser Glu Ser Gln Leu Pro Ser Lys Ile Pro Phe Gly Arg Tyr Val
 1               5                  10                  15

-continued

```
Phe Glu Arg Ile Lys Gln Val Gly Val Asn Thr Ile Phe Gly Val Pro
             20                  25                  30

Gly Asp Phe Asn Leu Ser Leu Leu Asp His Ile Tyr Thr Val Asp Gly
         35                  40                  45

Leu Arg Trp Ala Gly Asn Ala Asn Glu Leu Asn Ala Gly Tyr Ser Ala
 50                  55                  60

Asp Gly Tyr Ser Arg Ile Asn Gly Met Ser Cys Leu Val Thr Thr Phe
 65                  70                  75                  80

Gly Val Gly Asp Leu Ser Ala Val Asn Ala Ile Ala Gly Met Met Ala
                 85                  90                  95

Glu His Val Gly Cys Leu His Ile Val Gly Thr Pro Ser Leu Ser Ser
                100                 105                 110

Ile Ser Asn Arg Leu Leu Leu His His Thr Leu Gly Asn Gly Arg Phe
            115                 120                 125

Asp Ile Phe Glu Glu Met Ser Lys His Ile Thr Gln Lys Thr Ser Ser
        130                 135                 140

Ile Asp Asp Ile Arg Thr Ala Gln Ala Val Leu Asp Asp Leu Ile Glu
145                 150                 155                 160

Thr Ala Tyr Thr Thr Lys Arg Pro Val Tyr Leu Gly Leu Pro Ser Asn
                165                 170                 175

Phe Val Asp Gln Leu Val Asp Ser Glu Arg Leu Lys Thr Pro Leu Lys
            180                 185                 190

Leu Thr Leu Pro Pro Asn Asp Lys Leu Ala Glu Asp Glu Ile Val Glu
        195                 200                 205

Ser Ile Phe Asn Lys Ile Val Glu Ala Lys Asp Pro Ile Met Leu Val
210                 215                 220

Asp Ala Cys Ala Ser Arg His Asp Val Gln Asp Leu Val Ala Gln Phe
225                 230                 235                 240

Val Glu Ala Thr Lys Phe Pro Val Tyr Thr Thr Pro Met Gly Lys Ser
                245                 250                 255

Ala Phe Ser Glu Asp His Ser Arg Phe Gly Gly Val Tyr Ile Gly Val
            260                 265                 270

Leu Ser Asn Pro Asp Val Lys Glu Ala Val Glu Ser Ser Asp Leu Ile
        275                 280                 285

Leu Ser Val Gly Gly Leu Leu Ser Asp Phe Asn Thr Gly Ser Phe Ser
290                 295                 300

Tyr Asn Tyr His Thr Thr Asn Val Ile Glu Phe His Ser Asp Phe Cys
305                 310                 315                 320

Lys Val Arg Ala Ala Thr Tyr Ala Asp Val Lys Met Lys Tyr Val Leu
                325                 330                 335

Glu Arg Leu Cys Arg Lys Ile Lys Glu Ala Lys Leu Asp Tyr Val Pro
            340                 345                 350

Gln Pro Leu Pro Glu Ser Val Gln Asp Tyr Lys Lys Val Ala Asn Ile
        355                 360                 365

Lys Ser Gly Lys Leu Thr Gln Asp Tyr Leu Trp Lys Lys Leu Ser Phe
370                 375                 380

Phe Leu Arg Ser Gly Asp Val Leu Val Thr Glu Thr Gly Thr Ser Ser
385                 390                 395                 400

Phe Gly Val Thr Gln Thr His Phe Pro Gly Asn Ile Thr Ala Ile Ser
                405                 410                 415

Gln Val Leu Trp Gly Ser Ile Gly Tyr Ser Leu Pro Ser Ala Thr Gly
            420                 425                 430

Ala Gln Phe Ala Leu Glu Glu Ile Asp Pro Asn Arg Arg Cys Ile Leu
        435                 440                 445
```

```
Phe Ile Gly Asp Gly Ser Leu Gln Leu Thr Val Gln Ser Ile Ser Asp
            450                 455                 460

Ile Cys Arg Trp Asn Leu Lys Pro Tyr Leu Phe Val Leu Asn Asn Asn
465                 470                 475                 480

Gly Tyr Thr Ile Glu Lys Leu Ile His Gly Pro Lys Ala Gln Tyr Asn
            485                 490                 495

Met Ile Gln Lys Trp Asp His Phe Lys Ile Leu Glu Leu Phe His Asp
            500                 505                 510

Lys Val Asp Tyr Glu Asn His Arg Val Ser Thr Ile Glu Glu Leu Asn
            515                 520                 525

Ala Leu Phe Ala Asp Glu Ala Phe Asn Lys Asn Asp Lys Val Arg Leu
            530                 535                 540

Ile Glu Ile Met Leu Asp Glu Met Asp Ala Pro Glu Asn Leu Val Lys
545                 550                 555                 560

Gln Ala Lys Ile Ser Glu Gln Ile Asn Ala Ala
            565                 570

<210> SEQ ID NO 2
<211> LENGTH: 563
<212> TYPE: PRT
<213> ORGANISM: Kluyveromyces lactis

<400> SEQUENCE: 2

Met Ser Glu Ile Thr Leu Gly Arg Tyr Leu Phe Glu Arg Leu Lys Gln
1               5                   10                  15

Val Glu Val Gln Thr Ile Phe Gly Leu Pro Gly Asp Phe Asn Leu Ser
            20                  25                  30

Leu Leu Asp Asn Ile Tyr Glu Val Pro Gly Met Arg Trp Ala Gly Asn
            35                  40                  45

Ala Asn Glu Leu Asn Ala Ala Tyr Ala Ala Asp Gly Tyr Ala Arg Leu
        50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Val Ser Ser Gln Ala Lys Gln Leu Leu
            100                 105                 110

Leu His His Thr Leu Gly Asn Gly Asp Phe Thr Val Phe His Arg Met
            115                 120                 125

Ser Ser Asn Ile Ser Glu Thr Thr Ala Met Ile Thr Asp Ile Asn Thr
130                 135                 140

Ala Pro Ala Glu Ile Asp Arg Cys Ile Arg Thr Thr Tyr Val Ser Gln
145                 150                 155                 160

Arg Pro Val Tyr Leu Gly Leu Pro Ala Asn Leu Val Asp Leu Thr Val
            165                 170                 175

Pro Ala Ser Leu Leu Asp Thr Pro Ile Asp Leu Ser Leu Lys Pro Asn
            180                 185                 190

Asp Pro Glu Ala Glu Glu Val Ile Glu Asn Val Leu Gln Leu Ile
            195                 200                 205

Lys Glu Ala Lys Asn Pro Val Ile Leu Ala Asp Ala Cys Cys Ser Arg
210                 215                 220

His Asp Ala Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Lys His
            245                 250                 255
```

Pro Arg Phe Gly Gly Val Tyr Val Gly Thr Leu Ser Ser Pro Ala Val
            260                 265                 270

Lys Glu Ala Val Glu Ser Ala Asp Leu Val Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp Tyr Thr Lys Ile Arg Ser Ala Thr
305                 310                 315                 320

Phe Pro Gly Val Gln Met Lys Phe Ala Leu Gln Lys Leu Leu Thr Lys
                325                 330                 335

Val Ala Asp Ala Ala Lys Gly Tyr Lys Pro Val Pro Val Pro Ser Glu
            340                 345                 350

Pro Glu His Asn Glu Ala Val Ala Asp Ser Thr Pro Leu Lys Gln Glu
        355                 360                 365

Trp Val Trp Thr Gln Val Gly Glu Phe Leu Arg Glu Gly Asp Val Val
    370                 375                 380

Ile Thr Glu Thr Gly Thr Ser Ala Phe Gly Ile Asn Gln Thr His Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Arg Leu Ile
465                 470                 475                 480

His Gly Glu Thr Ala Gln Tyr Asn Cys Ile Gln Asn Trp Gln His Leu
                485                 490                 495

Glu Leu Leu Pro Thr Phe Gly Ala Lys Asp Tyr Glu Ala Val Arg Val
            500                 505                 510

Ser Thr Thr Gly Glu Trp Asn Lys Leu Thr Thr Asp Glu Lys Phe Gln
        515                 520                 525

Asp Asn Thr Arg Ile Arg Leu Ile Glu Val Met Leu Pro Thr Met Asp
    530                 535                 540

Ala Pro Ser Asn Leu Val Lys Gln Ala Gln Leu Thr Ala Ala Thr Asn
545                 550                 555                 560

Ala Lys Asn

<210> SEQ ID NO 3
<211> LENGTH: 1716
<212> TYPE: DNA
<213> ORGANISM: Hansenula polymorpha

<400> SEQUENCE: 3
atgtctgaat cccaactacc ttctaaaatt ccctttggcc gctacgtgtt tgagcgtatc      60
aagcaagtcg gagtgaacac cattttcggt gttcctggtg acttcaacct gtctctgctg     120
gaccacatct acactgtgga cggcctgaga tgggccggta acgccaacga gctcaatgcg     180
ggctattctg cggacggtta ctcccgtatc aacggcatgt cctgtctggt gaccaccttt     240
ggtgtcggcg acttatcggc agtcaatgcc attgcgggca tgatggccga gcacgttgga     300
tgtctgcaca ttgtcggcac gccttcgctc tccagtatct cgaacagact gctgctgcac     360

```
cacacactgg gtaacggccg gttcgacatt ttcgaggaga tgtccaagca catcacccag    420
aagacctcca gcatcgacga tattagaacg gcacaggctg ttctggacga cctgatcgag    480
accgcataca ccaccaagag accggtgtat ttgggactgc cttcgaactt tgtggaccag    540
ctggtcgact ccgagcggct caagacgcca ttgaagctga cccttcctcc aaacgacaag    600
cttgccgagg acgagattgt cgagagcatc ttcaacaaga ttgtcgaggc caaggaccca    660
attatgctgg tggatgcctg cgcttcgaga cacgatgtgc aggaccttgt ggcgcaattc    720
gtcgaggcca cgaaattccc cgtctacacc acgcctatgg gcaagtcggc cttcagcgag    780
gaccattcca gatttggcgg tgtgtacatc ggagttctgt cgaacccgga cgtgaaggag    840
gcggtcgagt cgtccgactt gatcctcagc gtcggcggcc tgctgtcgga cttcaacacg    900
ggctcgttct cgtacaacta ccacaccacc aacgtgatcg agttccactc cgacttctgt    960
aaagtgcgtg ctgccacgta cgcagacgtc aagatgaagt acgtcttgga gagactgtgc   1020
cgcaagatca aggaggccaa actgactac gtgccacagc cgctgccgga gtccgtccag    1080
gactacaaga aggtggccaa tatcaagtct ggcaagctga ctcaggacta cttgtggaaa   1140
aaactctcct ttttcctgcg ctctggcgac gttctggtca ccgagacagg cacgtcttcg   1200
ttcggtgtga cccagacgca tttcccaggc aacatcacgg ctatttccca ggttctgtgg   1260
ggctcgatcg gttattcgct tccttctgcc accggcgcgc aattcgcgct cgaggagatc   1320
gatcctaacc gcagatgtat tctgttcatt ggtgacggct ctttgcagct gaccgtccag   1380
tccatctcgg atatctgccg ctggaatctc aagccatatc tctttgtgct caacaacaac   1440
ggttacacga tcgagaagct gattcacggg cctaaggcac agtacaacat gatccagaaa   1500
tgggatcact tcaagattct cgagctgttc catgacaaag tcgactacga gaccaccgc    1560 gtgtcgacga tcgaggagct gaacgctctg tttgccgacg aggcctttaa caaaaacgac   1620
aaggtcagac tgatcgagat catgctcgac gagatggacg caccggagaa ccttgtcaag   1680
caagccaaga tctcggagca gatcaatgca gcttaa                               1716
```

```
<210> SEQ ID NO 4
<211> LENGTH: 1692
<212> TYPE: DNA
<213> ORGANISM: Kluyveromyces lactis

<400> SEQUENCE: 4
```

```
atgtctgaaa ttacattagg tcgttacttg ttcgaaagat taaagcaagt cgaagttcaa     60
accatctttg gtctaccagg tgatttcaac ttgtccctat tggacaatat ctacgaagtc    120
ccaggtatga gatgggctgg taatgccaac gaattgaacg ctgcttacgc tgctgatggt    180
tacgccagat taaagggtat gtcctgtatc atcaccacct tcggtgtcgg tgaattgtct    240
gctttgaacg gtattgccgg ttcttacgct gaacacgttg gtgtcttgca cgttgtcggt    300
gttccatccg tctcttctca agctaagcaa ttgttgttgc accacacctt gggtaacggt    360
gacttcactg ttttccacag aatgtcctcc aacatttctg aaaccactgc tatgatcacc    420
gatatcaaca ctgccccagc tgaaatcgac agatgtatca gaaccactta cgtttcccaa    480
agaccagtct acttgggttt gccagctaac ttggtcgact tgactgtccc agcttctttg    540
ttggacactc caattgattt gagcttgaag ccaaatgacc agaagccga agaagaagtc    600 atcgaaaacg tcttgcaact gatcaaggaa gctaagaacc cagttatctt ggctgatgct    660
tgttgttcca gacacgatgc caaggctgag accaagaagt tgatcgactt gactcaattc    720 ccagcctcg ttacccccaat gggtaagggt tccattgacg aaaagcaccc aagattcggt    780
```

```
ggtgtctacg tcggtaccct atcttctcca gctgtcaagg aagccgttga atctgctgac    840
ttggttctat cggtcggtgc tctattgtcc gatttcaaca ctggttcttt ctcttactct    900
tacaagacca agaacattgt cgaattccac tctgactaca ccaagatcag aagcgctacc    960
ttcccaggtg tccaaatgaa gttcgcttta caaaaattgt tgactaaggt tgccgatgct   1020
gctaagggtt acaagccagt tccagttcca tctgaaccag aacacaacga agctgtcgct   1080
gactccactc cattgaagca agaatgggtc tggactcaag tcggtgaatt cttgagagaa   1140
ggtgatgttg ttatcactga accggtacc  tctgccttcg gtatcaacca aactcatttc   1200
ccaaacaaca catacggtat ctctcaagtt ttatggggtt ccattggttt caccactggt   1260
gctaccttgg gtgctgcctt cgctgccgaa gaaattgatc caaagaagag agttatctta   1320
ttcattggtg acggttcttt gcaattgact gttcaagaaa tctccaccat gatcagatgg   1380
ggcttgaagc catacttgtt cgtattgaac aacgacggtt acaccattga aagattgatt   1440
cacggtgaaa ccgctcaata caactgtatc caaaactggc aacacttgga attattgcca   1500
actttcggtg ccaaggacta cgaagctgtc agagtttcca ccactggtga atggaacaag   1560
ttgaccactg acgaaaagtt ccaagacaac accagaatca gattgatcga agttatgttg   1620
ccaactatgg atgctccatc taacttggtt aagcaagctc aattgactgc tgctaccaac   1680
gctaagaact aa                                                       1692

<210> SEQ ID NO 5
<211> LENGTH: 625
<212> TYPE: DNA
<213> ORGANISM: Hansenula polymorpha

<400> SEQUENCE: 5
caattatcat taataatcac tcatgatccc tgcgtctaga ggttggtcta gaccacatcc     60
gtgcaccaga caagacacgg cccacggagg taaaggtgcc aactcgcaaa gtgcaacaac    120
catggctctc cagcacggtg cgtggggtaa agacaatctc cgggaaccga tcccgaaacc    180
gagaaagagg gttttaagcg tgtgtccttt gcggaggcgg tgtagcactt cttattgtcc    240
tttgggccgc tccggcggtt gagcttccac agaacatcct tgcacggaca agcagtcccg    300
gagacgccat gttgggtgat acccacttct ggctgtacag agctttatat caccttacct    360
ggcgctagag tagacccaat tcccgactca caccacccctc acatgcagaa ctaaccaata    420
aggtaattaa ttaacacgat atagctcgtg gtgaacactg gcccggagta gtcatacgtg    480
taggtttttg gcgtgatgaa aatcaggtgg agcacgactt tcgtaatgt tcgggaggga    540
gtgctgcaaa cggtatataa ggaccagttt ttctcgcaac attatcaatt gctctttagt    600
acaaagataa tatagaaaca aaatg                                          625

<210> SEQ ID NO 6
<211> LENGTH: 1276
<212> TYPE: DNA
<213> ORGANISM: Hansenula polymorpha

<400> SEQUENCE: 6
aagcttggag acgtggaagg acataccgct tttgagaagc gtgtttgaaa atagttcttt     60
ttctggttta tatcgtttat gaagtgatga gatgaaaagc tgaaatagcg agtataggaa    120
aatttaatga aaattaaatt aaatattttc ttaggctatt agtcaccttc aaaatgccgg    180
ccgcttctaa gaacgttgtc atgatcgaca actacgactc gtttacctgg aacctgtacg    240
agtacctgtg tcaggaggga gccaatgtcg aggttttcag gaacgatcag atcaccattc    300
```

```
cggagattga gcagctcaag ccggacgttg tggtgatatc ccctggtcct ggccatccaa      360
gaacagactc gggaatatct cgcgacgtga tcagccattt aaaggcaag attcctgtct       420 ttggtgtctg tatgggccag cagtgtatct tcgaggagtt tggcggagac gtcgagtatg     480
cgggcgagat tgtccatgga aaaacgtcca ctgttaagca cgacaacaag ggaatgttca     540
aaaacgttcc gcaagatgtt gctgtcacca gataccactc gctggccgga acgctcaagt    600
cgcttccgga ctgtctagag atcactgctc gcacagacaa cgggatcatt atgggtgtga   660
gacacaagaa gtacaccatc gagggcgtcc agtttcatcc agagagcatt ctgaccgagg    720
agggccatct gatgatccag aatatcctca acgtttccgg tggttactgg gaggaaaatg    780
ccaacggcgc ggctcagaga aaggaaagca tattggagaa aatatacgcg cagagacgaa    840
aagactacga gtttgagatg aacagaccgg ggcgcagatt tgctgatcta gaactgtact    900
tgtccatggg actggcaccg ccgctaatca atttttacga cagattggag cagaacatca   960
gcgccggcaa ggttgcaatt ctcagcgaaa tcaagagagc gtcgccttct aaaggcgtca   1020
tcgacggaga cgctaacgct gccaaacagg ccctcaacta cgccaaggct ggagttgcca   1080
caatttctgt tttgaccgag ccaccctggt ttaaaggaaa tatccaggac ctggaggtgg   1140
ccagaaaagc cattgactct gtggccaata gaccgtgtat tttgcggaag gagtttatct   1200
tcaacaagta ccaaattcta gaggcccgac tggcgggagc agacacggtt ctgctgattg   1260
tcaagatgct gagctc                                                    1276
```

<210> SEQ ID NO 7
<211> LENGTH: 26
<212> TYPE: DNA
<213> ORGANISM: artificial sequence
<220> FEATURE:
<223> OTHER INFORMATION: PCR Primer

<400> SEQUENCE: 7
cgccatatgt ctgaatccca actacc                                         26

<210> SEQ ID NO 8
<211> LENGTH: 30
<212> TYPE: DNA
<213> ORGANISM: artificial sequence
<220> FEATURE:
<223> OTHER INFORMATION: pcr primer

<400> SEQUENCE: 8
tttgcggccg cttaagctgc attgatctgc                                     30

<210> SEQ ID NO 9
<211> LENGTH: 29
<212> TYPE: DNA
<213> ORGANISM: artificial sequence
<220> FEATURE:
<223> OTHER INFORMATION: PCR primer

<400> SEQUENCE: 9
gcgaagctta tgtctgaaat tacattagg                                      29

<210> SEQ ID NO 10
<211> LENGTH: 29
<212> TYPE: DNA
<213> ORGANISM: artificial sequence
<220> FEATURE:
<223> OTHER INFORMATION: PCR Primer

<400> SEQUENCE: 10

-continued

```
cataagcttt tagttcttag cgttggtag                                    29

<210> SEQ ID NO 11
<211> LENGTH: 32
<212> TYPE: DNA
<213> ORGANISM: Artificial Sequence
<220> FEATURE:
<223> OTHER INFORMATION: PCT Primer

<400> SEQUENCE: 11
gcgggcgccc caattatcat taataatcac tc                                32

<210> SEQ ID NO 12
<211> LENGTH: 29
<212> TYPE: DNA
<213> ORGANISM: artificial sequence
<220> FEATURE:
<223> OTHER INFORMATION: PCR Primer

<400> SEQUENCE: 12
taaggcgcca gcatcttgac aatcagcag                                    29

<210> SEQ ID NO 13
<211> LENGTH: 34
<212> TYPE: DNA
<213> ORGANISM: artificial sequence
<220> FEATURE:
<223> OTHER INFORMATION: PCR Primer

<400> SEQUENCE: 13
cggctgcagg agaacttcta gtatatctac atac                              34

<210> SEQ ID NO 14
<211> LENGTH: 32
<212> TYPE: DNA
<213> ORGANISM: Artificial Sequence
<220> FEATURE:
<223> OTHER INFORMATION: PCR Primer

<400> SEQUENCE: 14
tatctgcagc tacgtcgtta aggccgtttc tg                                32
```

INCREASED ETHANOL PRODUCTION FROM XYLOSE

CROSS-REFERENCE TO RELATED APPLICATIONS

This application claims priority to U.S. Provisional Patent Application No. 60/923,605, filed on Apr. 16, 2007. That application is incorporated by reference as if fully rewritten herein.

BACKGROUND OF THE INVENTION

1. Field of the Invention

The present invention relates to methods and compositions for the fermentative production of ethanol from D-xylose using yeast.

2. Background

Metabolic engineering of microorganisms is often an effective means to produce commercially a number of chemicals that may be used for multiple applications (see, e.g., Lee, S. Y., et al. *Macromol. Biosci.* 4:157-164 (2004)). One chemical that has garnered much interest is ethanol. Although ethanol has a number of uses, it is most commonly used as a fuel additive. As a fuel additive, ethanol is a low value product with much of the cost of its production attributed to the cost of raw materials. It would be desirable, therefore, to develop ethanologens and fermentation processes for the production of ethanol from readily available, inexpensive starting materials. These starting materials may be, for example, lignocellulosics. These lignocellulosics may be derived from renewable biomass waste streams from food, paper pulping operations, agricultural residues and recycled paper from municipalities.

The major constituent of plant biomass is lignocellulose. Upon hydrolysis, lignocellulose yields a mixture of monomeric hexoses (glucose, mannose and galactose) and pentoses (D-xylose and L-arabinose). Among these, glucose is the most abundant, followed by xylose and mannose with other sugars present in much lower concentrations. Fermentation of both glucose and xylose is currently regarded as a high priority for economical conversion of biomass into ethanol. Most microorganisms are able to ferment glucose but few have been reported to utilize xylose efficiently and even fewer ferment this pentose to ethanol. However, the competitive process for fuel ethanol production from lignocellulosic material requires the development of microbes capable of active xylose fermentation.

Lignocellulose is approximately 30% D-xylose (see Ryabova, O. B., et al. "Xylose and Cellobiose Fermentation to Ethanol by the Thermotolerant Methylotrophic Yeast *Hansenula polymorpha*," *FEMS Yeast Res.* 4:157-164 (2003)). Xylose is a "wood sugar" with the IUPAC designation (2S,3R,4S,5R)-oxane-2,3,4,5-tetrol.

Only a relatively small number of wild type microorganisms can ferment D-xylose. These microorganisms are generally not suitable for large-scale fermentation. This unfavorability may arise, for example, as a result of unfamiliarity with the microorganisms, difficulty obtaining the microorganisms, poor productivity and/or growth on pretreated lignocellulosics or unsatisfactory yield when grown on mixed sugars derived from biomass.(C. Abbas, "Lignocellulosics to ethanol: meeting ethanol demand in the future," The Alcohol Textbook, 4th Edition. (K. A. Jacques, T. P. Lyons and D. R. Kelsall, eds). Nottingham University Press, Nottingham, UK, 2003, pp. 41-57.; C. Abbas, "Emerging biorefineries and biotechnological applications of nonconventional yeast: now and in the future," The Alcohol Textbook, 4th Edition. (K. A. Jacques, T. P. Lyons and D. R. Kelsall, eds). Nottingham University Press, Nottingham, United Kingdom, 2003, pp. 171-191).

Yeasts are considered the most promising microorganisms for alcoholic fermentation of xylose (see Ryabova, supra). They have larger cells than bacteria, are more resistant to viral infection, and tend to be more resistant to negative feedback from ethanol. Furthermore, yeast growth and metabolism have been extensively studied for a number of species.

A number of yeasts are known to naturally ferment D-xylose. These include *Pichia stipitis, Candida shehatae*, and *Pachysolen tannophilus* (see Ryabova, supra; Cite 2, C. Abbas 2003). The common brewer's yeast *Saccharomyces cerevisiae* is not known to ferment D-xylose naturally, but a number of strains of metabolically engineered *S. cerevisiae* that do ferment D-xylose have been reported.

Numerous studies have described the metabolism of D-xylose by recombinant *S. cerevisiae* (see, e.g., Wahlbom, et al., "Metabolic Engineering for Improved Xylose Utilization of *Saccharomyces Cerevisiae*," U.S. Pat. Pub. No. 2005/0153411A1 (Jul. 14, 2005); Griffin, et al., "Method of Processing Lignocellulosic Feedstock for Enhanced Xylose and Ethanol Production," U.S. Pat. Pub. No. 2004/0231661A1 (Nov. 25, 2004); Gong, C-S, "Direct Fermentation of D-Xylose to Ethanol by a Xylose-Fermenting Yeast Mutant," U.S. Pat. No. 4,368,268 (Jan. 11, 1983); Hallbom, J., et al., "Production of Ethanol from Xylose" U.S. Pat. No. 6,582,944 (Jun. 24, 2003); Jeffries, T. W, et al., "Xylose-Fermenting Recombinant Yeast Strains," U.S. Pat. Pub. No. 2004/0142456A1 (Jul. 22, 2004); Jeffries, T. W. & Jin, Y-S., "Metabolic Engineering for Improved Fermentation of Pentoses by Yeasts" *Appl. Microbiol. Biotechnol.* 63: 495-509 (2004); Jin, Y-S. & Jeffries, T. W., "Stoichiometric Network Constraints on Xylose Metabolism by Recombinant *Saccharomyces cerevisiae*" *Met. Eng.* 6: 229-238 (2004); Pitkanen, J-Y., "Impact of Xylose and Mannose on Central Metabolism of Yeast *Saccharomyces cerevisiae*" Helsinki Univ. of Tech., Dept. of Chem. Tech., Technical Biochemistry Report (January 2005); Porro, D., et al., "Replacement of a Metabolic Pathway for Large-Scale Production of Lactic Acid from Engineered Yeasts" *App. & Env. Microbiol.* 65(9): 4211-4215 (1999); Jin, Y-S., et al., "*Saccharomyces cerevisiae* Engineered for Xylose Metabolism Exhibits a Respiratory Response" *App. & Env. Microbiol.* 70(11): 6816-6825 (2004); Sybirna, K, et al., "A New *Hansenula polymorpha* HAP4 Homologue which Contains Only the N-Terminal Conserved Domain of the Protein is Fully Functional *Saccharomyces cerevisiae*" *Curr. Genetics* 47(3): 172-181 (2005); Toivari, M. H., et al., "Conversion of Xylose to Ethanol by recombinant *Saccharomyces cerevisiae*: Importance of Xylulokinase (XKS1) and Oxygen Availability" *Metabolic Eng.* 3:236-249 (2001).

As shown in FIG. 1, D-Xylose metabolism in yeast proceeds along a pathway similar to that of glucose via pentose phosphate pathway. Carbon from D-xylose is processed to ethanol via the glycolytic cycle or to $CO_2$ via respiratory TCA cycle.

Fermentation to ethanol relies in part on the metabolism of pyruvate, which is a metabolite that may be used in either respiration or fermentation (see van Hoek, P., et al., "Effects of Pyruvate Decarboxylase Overproduction on Flux Distribution at the Pyruvate Branch Point in *Saccharomyces cerevisiae*," *Appl. & Enviro. Microbiol.* 64(6); 2133-2140 (1998)). Pyruvate enters fermentation following decarboxylation of pyruvate to acetaldehyde by the enzyme pyruvate decarboxylase (E.C. 4.1.1.1). Pyruvate decarboxylase is a member of the family of biotin-dependent carboxylases. It catalyzes the decarboxylation of pyruvate to form oxaloacetate with ATP cleavage. The oxaloacetate can be used for synthesis of fat, glucose, and some amino acids or other derivatives. The enzyme is highly conserved and found in a variety of prokaryotes and eukaryotes.

Pyruvate decarboxylase was first reported by (Utter, M. F., et al., "Formation of oxaloacetate from pyruvate and $CO_2$." *J. Biol. Chem.* 235:17-18 (1960)) while defining the gluconeogenic pathway in chicken liver. Attempts to overexpress the PDC1 gene in *S. cerevisiae* did not resulted in higher ethanol yield from glucose (Schaaff I, Heinisch J & Zimmermann F K (1989) "Overproduction of glycolytic enzymes in yeast." *Yeast* 5(4): 285-290; van Hoek P, Flikweert M T, van der Aart Q J, Steensma H Y, van Dijken J P & Pronk J T (1998) "Effects of pyruvate decarboxylase overproduction on flux distribution at the pyruvate branch point in *Saccharomyces cerevisiae*." *Appl Environ Microbiol* 64(6): 2133-2140.)

It has been proposed that one bottleneck involved in D-xylose fermentation is the hydrolysis of xylan, which is the major component of hemicellulose to monosaccharides (see Ryabova, supra). One approach to overcoming this bottleneck is by using "simultaneous saccharification and fermentation" (SSF). This is a process in which pretreated lignocellulose is hydrolyzed by cellulases and hemicellulases while the hexoses and pentoses produced by this hydrolysis (including xylose) are fermented to ethanol. This would allow continuous conversion of the sugars to ethanol, preventing their accumulation in the medium.

A drawback of SSF is the difference in the optimal temperature at which cellulases and hemicellulases are active (at least about 50° C.) that are compatible with the optimal temperature for yeast growth and fermentation of xylose (about 30° C.). One solution to this drawback is to perform SSF using the thermotolerant methylotrophic yeast *Hansenula polymorpha* (also known as *Pichia angusta*). This yeast has been reported to have optimum and maximum growth temperatures of 37° C. and 48° C., respectively. These temperatures are higher than those tolerated by most other ethanol producing yeasts (Ryabova, et al.). Furthermore, Ryabova, et al. reported that under some conditions *H. polymorpha* is able to naturally ferment D-xylose (see also Voronovsky, A. Y., et al., "Expression of xylA Genes Encoding Xylose Isomerases From *Escherichia coli* and *Streptomyces coelicolor* in the Methylotrophic Yeast *Hansenula polymorpha*" *FEMS Yeast Res.* 5(11): 1055-62 (2005)).

Therefore it would be advantageous to develop strains of *H. polymorpha* with an increased ability to produce ethanol from lignocellulosic starting materials, including the C5 sugar, D-xylose.

SUMMARY OF THE INVENTION

Provided herein are genes and genetic elements useful in modifying host cells. These host cells may include, for example, microorganisms. One particularly suitable microorganism for use in embodiments of the invention is the yeast *H. polymorpha*. Methods and compositions of the invention are useful for providing microorganisms with increased enzyme activity. In one embodiment, a *H. polymorpha* host cell overexpresses pyruvate decarboxylase.

A further embodiment provides a process for production of ethanol, including isolating from donor yeast a first polynucleotide encoding a polypeptide that has pyruvate decarboxylase activity in *H. polymorpha*. Polypeptides that may be encoded may include an amino acid from the group consisting of the amino acid sequence of SEQ ID NO: 1 or SEQ ID NO: 2 or a fragment of either, or an amino acid sequence at least 95% identical to SEQ ID NO: 1 and/or SEQ ID NO: 2, wherein the polypeptide has pyruvate decarboxylase activity.

The process further includes constructing yeast vectors including the polynucleotide, transforming a host cell with the vectors obtained in step (b) to obtain a recombinant yeast strain; cultivating the recombinant yeast strain in a xylose-containing medium; and isolating and purifying ethanol formed in said medium. In another embodiment, the first polynucleotide has a sequence selected from SEQ ID NO: 3 (FIG. 2), SEQ ID NO: 4 (FIG. 3), or sequences at least 95% identical to SEQ ID NO: 3 and/or SEQ ID NO:4.

In a further embodiment, the vectors further include a promoter operably associated with said first polynucleotide. In a yet still further embodiment, the promoter is selected from, for example, promoters of the GAP, PMA1, TEF1 genes of *H. polymorpha*. In a preferred embodiment, the promoter is a *Hansenula polymorpha* glyceraldehyde-3-phosphate dehydrogenase gene promoter (HpGAP). The HpGAP promoter may have the nucleotide sequence of SEQ ID NO: 5 (FIG. 4).

In another embodiment of the invention, the vector further includes a terminator operably associated with the first polynucleotide. The terminator is selected, for example, from the group including terminators of the GAP, PMA1, TEF1, AOX genes of *H. polymorpha*. In a preferred embodiment, the terminator is a *Hanselula polymorpha* alcohol oxidase terminator. The AOX terminator may have the nucleotide sequence of SEQ ID NO: 6 (FIG. 5).

Another embodiment of the invention includes an isolated polynucleotide encoding a polypeptide including the amino acid sequence of SEQ ID NO: 1 or a fragment thereof, the amino acid sequence of SEQ ID NO: 2 or a fragment thereof or an amino acid sequence at least 95% identical to SEQ ID NO: 1 and or SEQ ID NO: 2, wherein the polypeptide has pyruvate decarboxylase activity.

The polynucleotide may include a promoter that controls expression of said polypeptide. The promoter may be, for example, a promoter of the GAP, PMA1, TEF1 genes. In a preferred embodiment the promoter is a *Hansenula polymorpha* glyceraldehyde-3-phosphate dehydrogenase promoter. The HpGAP promoter may have the nucleotide sequence of SEQ ID NO:5.

Polynucleotides of the invention may further include a terminator. The terminator may be, for example, a member of the group including terminators of the GAP, PMA1, TEF1, AOX genes. In a preferred embodiment, the terminator is a *Hanselula polymorpha* alcohol oxidase terminator. The AOX terminator may have the polynucleotide sequence of SEQ ID NO:6.

Embodiments of the invention also include vectors and plasmids including polynucleotides of the invention. Embodiments of the invention further include one or more isolated host cells including plasmids that contain polynucleotides of the invention. The isolated host cell may be, for example, a strain of *Hansenula polymorpha*. Embodiments of the invention also include production of ethanol from a lignocellulosic starting material by culturing host cells of the invention in a medium including lignocellulosic starting material. Host cells of the invention may also be cultivated in a medium containing xylose but without other lignocellulosic materials.

In one embodiment, an isolated polynucleotide is provided, comprising a promoter operably associated with an open reading frame (ORF) and a terminator. In one particular embodiment, the promoter is the *H. polymorpha* GAP promoter (the promoter of the glyceraldehyde-3-phosphate dehydrogenase gene) (SEQ ID NO: 5), the ORF is the *H. polymorpha* PDC1 gene (SEQ ID NO: 3) or the *Kluyveromyces lactis* PDC1 gene (SEQ ID NO: 4), and the terminator is the AOX terminator (the terminator of the *H. polymorpha* alcohol oxidase gene) (SEQ ID NO: 6). In other embodiments, the promoter may be selected from the *H. polymorpha* TEF1, or GAP, or PMA1 promoters, the ORF is selected from the *H. polymorpha* PDC1 gene (SEQ ID NO: 3), nucleotide fragments including the *H. polymorpha* PDC1 gene, and polynucleotides including nucleotide sequences at least 95% identical to the PDC1 gene that encode polypeptides that have pyruvate decarboxylase activity in *H. polymorpha*.

The ORF may also be selected from the *K. lactis* PDC1 gene (SEQ ID NO: 4), nucleotide fragments including the *K. lactis* PDC1 gene, and polynucleotides including nucleotide sequences at least 95% identical to the *K. lactis* PDC1 gene that have pyruvate decarboxylase activity in *H. polymorpha*.

Polynucleotides of the invention may be contained within a vector and/or host cell. In particular, plasmids including polynucleotides of the invention are provided. Also provided are methods of integrating the polynucleotides into the genome of a host cell.

Another embodiment provides a method for fermentative production of ethanol from a starting material including xylose. Another embodiment provides a method for manipulating carbon flux in a yeast cell comprising culturing a yeast cell containing a polynucleotide of the invention and recovering ethanol from a culture medium.

BRIEF DESCRIPTION OF THE SEVERAL VIEWS OF THE DRAWINGS

FIG. 1 is a scheme of xylose and glucose metabolism in yeasts.

FIG. 2 shows a sequence of the *H. polymorpha* PDC1 ORF (SEQ ID NO: 3).

FIG. 3 shows a sequence of the *Kluyveromyces lactis* PDC1 ORF (SEQ ID NO: 4).

FIG. 4 shows a promoter sequence of the *H. polymorpha* glyceraldehyde 3-phosphate dehydrogenase gene (HpGAP) (SEQ ID NO: 5).

FIG. 5 demonstrates a terminator sequence of the *H. polymorpha* alcohol oxidase gene (HpAOX) (SEQ ID NO: 6).

FIG. 14 shows the RT-PCR of *H. polymorpha* aldehyde dehydrogenase genes. RT-PCR reaction on cDNA of *H. polymorpha* strains, 1—3Leu+, control strain, Leu+ transformant; 2—2EthOH—. Primers were used for ORF116, 168, 226, 313, 529 selected on the basis of blast results against ALD6 *S. cerevisiae*. Primers for actin (ACT1) were used as a control.

FIG. 17 shows the ethanol production and biomass accumulation during xylose fermentation at 48° C. Transformants: a1—2EthOH—, a2—2EthOH-/pGLG61+PDC1Hp-12, a3—2EthOH-/pGLG61+PDC1Hp-13, a4—2EthOH-/ploxZeoloxPDC1Hp-10.

DETAILED DESCRIPTION OF THE INVENTION

Figure 6:
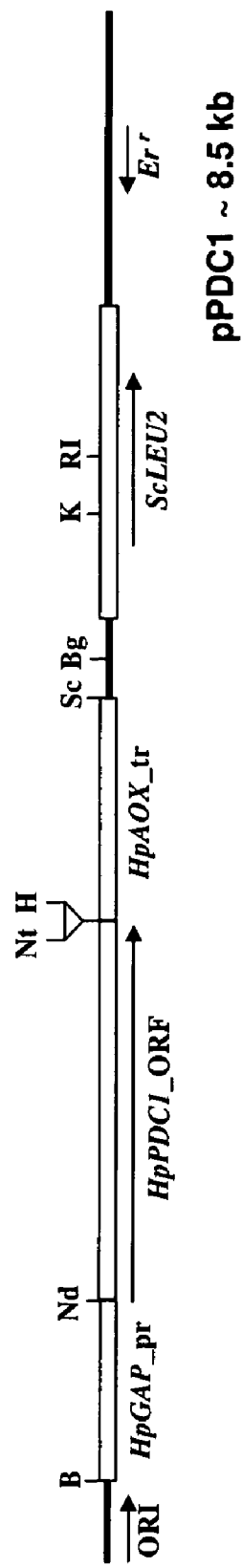
FIG. 6 shows a linear map of recombinant plasmid pPDC1.

As used herein, the singular forms "an," "a," and "the" used in the specification and claims include both singular and plural unless the content clearly dictates otherwise. In particular, those skilled in the art will recognize that while design and creation of catalytic materials and catalytic supports are described in terms of a single cell, more effective systems will include one or more cells each expressing one or more receptor proteins.

Provided herein are methods and compositions of matter useful in the manipulation of carbon flux in microorganisms, preferably in members of the *Hansenula* (*Pichia*) genus, and most preferably in *H. polymorpha* (*P. angusta*). As a non-limiting example, the manipulation of flux related to the carbon flow of pyruvate in *H. polymorpha* (*P. angusta*) is facilitated by the methods and compositions of matter included herein.

It is to be understood that certain descriptions of the embodiments of the invention have been simplified to illustrate only those elements and limitations that are relevant to a clear understanding of the present invention, while eliminating, for the purposes of clarity, other elements. Those of ordinary skill in the art, upon considering the present description, will recognize that other elements and/or limitations may be desirable to implement embodiments of the invention. Because such other elements and/or limitations may be ascertained by one of ordinary skill in the art upon considering the present description, and are not necessary for a complete understanding of the embodiments, a discussion of such elements and limitations is not provided herein. Still, the description set forth herein is not intended to limit the scope of the claims.

By the term "gene" is meant a segment of nucleic acid, DNA or RNA, which encodes and is capable of expressing a specific gene product. A gene often produces a protein or polypeptide as its gene product, but in its broader sense, a gene can produce any desired product, whether the product is a protein, polypeptide or nucleic acid. Functional or structural nucleic acid, such as, without limitation, rRNA, ribozymes, antisense RNA or interfering RNA (e.g., siRNA) also may be considered "gene products."

A "gene" contains an "expressed sequence" that can encode not only a protein or polypeptide, but a structural or functional nucleic acid, such as an antisense or siRNA. A gene may also contain sequences containing regulatory elements, such as, without limitation, promoters, enhancers and terminators; such regulatory elements may be "operably linked," most typically in an appropriate proximity to each other. Such promoters operate in cis (attached to each other on the same nucleic acid molecule) to cause expression of "a gene product." The choice of gene constituents, such as the particular combination of regulatory elements and expressed sequence, will dictate the conditions of expression. For example, a constitutive promoter, such as the TEF1 (translation elongation factor 1A gene) promoter, coupled to an expressed sequence will cause constitutive expression of the expressed sequence when transferred into a suitable host cell. A "constitutive promoter" is an unregulated promoter that allows for continual transcription of its associated gene. A promoter is considered constitutive if it functions to promote transcription of a gene under normal growth conditions. A constitutive promoter typically is not substrate specific and does not vary substantially in its expression under normal growth conditions.

A "gene" can include introns or other DNA sequences that can be spliced from the final RNA transcript. An expressed DNA sequence that encodes a protein or peptide ("protein encoding sequence") includes an open reading frame (ORF). The protein encoding sequence may comprise intervening introns. Further, the term "gene" includes expressed sequences as well as non-expressed sequences. All DNA sequences provided herein are understood to include complementary strands unless otherwise noted. Furthermore, RNA sequences can be prepared from DNA sequences by substituting uracil for thymine, and are included in the scope of this definition and invention, along with RNA copies of the DNA sequences of the invention isolated from cells.

By the term "oligonucleotide" is meant a nucleic acid of from about 7 to about 50 bases though they are more typically from about 15 to about 35 bases. Oligonucleotides are useful as probes or primers for use in hybridization or amplification assays such as Southern or Northern blots; molecular beacon; polymerase chain reaction (PCR); reverse transcriptive PCR (RT-PCR); quantitative RT-PCR (QRT-PCT), e.g., TAQ-MAN; isothermal amplification methods, such as NASBA (nucleic acid sequence-based amplification); and rolling circle amplification, including use of padlock probes. Oligonucleotides of the invention can be modified by the addition of peptides, labels (including fluorescent, quantum dot, or enzyme tags), and other chemical moieties and are understood to be included in the scope of this definition and the invention.

As used herein, in the context of the novel nucleotide sequences described herein, a nucleic acid is "specific to" a given sequence, such as the pyruvate decarboxylase cDNA and genomic sequences provided, if it can hybridize specifically to a given sequence under stringent conditions, such as, without limitation, 0.2×SSC at 65° or in a PCR reaction under typical reaction (annealing) temperatures. Typically, one sequence is "specific" to a reference sequence if the nucleic acid has 90 to 100% homology (sequence identity) to the reference sequence.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches. Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, as modified in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mouth View, Calif.); the ALIGN program (Version 2.0) and GAP, BESTFIT, BLAST, FASTA, and TFASTA in the CGC Wisconsin Genetics Software Packages, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244; Higgins et al. (1989) CABIOS 5:151-153; Corpet et al. (1988) *Nucleic Acids Res.* 16:10881-90; Huange et al. (1992) CABIOS 8:155-65; and Pearson et al. (1994) *Meth. Mol. Biol.* 24:307-331. The ALIGN program is based on the algorithm of Myers and Miller (1988) supra. A PAM 120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra.

BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=5, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, and PSI-BLAST, the default parameters of the respective programs (e.g., BLASTN for nucleotide sequences, BLASTX for proteins) can be used. See the National Center for Biotechnology Information web site on the world wide web at ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nswgapdna.cmp scoring matrix; or any equivalent program thereof.

By "equivalent program" is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts.

If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Packages for protein sequences are 8 and 2, respectively. For nucleotide sequences, the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Packages is BLOSUM62 (see Henikoff and Henikoff (1989) *Proc. Natl. Acad. Sci. USA* 89: 10915).

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters.

In the context of the sequences provided herein, a sequence is specific to that reference sequence if, under any given reaction condition that can be used to distinguish one sequence from another, such as, without limitation, PCR, Southern blot or Northern blot, but not to other sequences, such as sequences from other species including without limitation those of *S. cerevisiae*, *A. niger*, *A. terreus*, *P. pastoris*, and *S. pombe*. Thus, in a nucleic acid detection assay, a probe/primer is "specific to" a sequence if it can bind to a specific transcript or desired family of transcripts extracted from a specimen, to the practical inclusion (i.e., does not interfere substantially with the detection assay) of other sequences. In a PCR assay, primers are specific to a reference sequence if they specifically amplify a portion of that sequence, to the practical exclusion of other sequences in a sample.

As used herein, a "primer" or "probe" for detecting a specific nucleic acid species is any primer, primer set, and/or probe that can be utilized to detect and/or quantify the specific nucleic acid species. A "nucleic acid species" can be a single nucleic acid species, corresponding to a single gene, or can be nucleic acids that are detected by a single common primer and/or probe combination.

By the term "host cell" is meant any prokaryotic or eukaryotic cell where a desired nucleic acid sequence has been introduced into the cell. The metabolic processes and pathways of such a host cell are capable of maintaining, replicating, and/or expressing a vector containing a foreign gene or DNA molecule. There are a variety of suitable host cells, including but not limited to bacterial, fungal, insect, mammalian, and plant cells, that can be utilized in various ways (for example, as a carrier to maintain a plasmid comprising a desired sequence). Representative microbial host cells include, but are not limited to, fungal cells such as *Rhizopus* sp., *Saccharomyces* sp., *Streptomyces* sp., *Pichia* sp., *Aspergillus* sp., and bacterial cells such as *Lactobacillus* sp., *Escherichia* sp., *Corynebacterium* sp., *Brevibacterium* sp., *Pseudomonas* sp., *Proteus* sp., *Enterobacter* sp., *Citrobacter* sp., *Erwinia* sp., *Xanthomonas* sp., *Flavobacterium* sp., *Streptococcus* sp., *Lactococcus* sp., *Leuconostoc* sp., and *Enterococcus* sp. In one embodiment, the host cell is *Hansenula polymorpha* (*Pichia angusta*). In another embodiment, the host cell is *Escherichia coli*. In a yet still further embodiment, the host cell is *Saccharomyces cerevisiae*.

By the term "polynucleotide" is meant any single-stranded sequence of nucleotide, connected by phosphodiester linkages, or any double-stranded sequences comprising two such complementary single-stranded sequences held together by hydrogen bonds. Unless otherwise indicated, each polynucleotide sequence set forth herein is presented as a sequence of deoxyribonucleotides (abbreviated A, G, C and T). The term "polynucleotide" encompasses DNA molecules or polynucleotide, sequences of deoxyribonucleotides, and RNA molecules or polyribonucleotides and combinations thereof.

By the term "promoter" is meant a DNA sequence within a larger DNA sequence that provides or defines a site to which RNA polymerase can bind and initiate transcription. The promoters described herein can be used to over-express or up-regulate, for example, and without limitation, genes encoding enzymes that increase carbon flux to lactic acid, fumarate, and other desired metabolites during changes in fermentation conditions.

By the term "carbon flux" is meant the biochemical pathway by which carbon is metabolized in an organism. A change in carbon flux, therefore, is a change in the metabolic processing of carbon in response to a change in the organism or its environment. Carbon flux may be changed in any manner, including but not limited to changing the environment of the organism, such as limiting oxygen and/or changing the expression of genes and gene products in the organism (e.g., introducing heterologous gene sequences).

An "equivalent" of a given reference nucleotide sequence or element contained therein is a nucleotide sequence containing, as compared to the reference nucleotide sequence, all elements of that reference nucleotide sequence, such that the characteristic function of that reference nucleic acid or peptide is retained. Those of skill in the art understand that a functional protein may be encoded by equivalent DNA sequences due to degeneracy in the genetic code. For example, one codon may be substituted for another, yet encode the same amino acid, such as, for example and without limitation, in reference to the Ala codon, the substitution of GCG for GCA. In the case of proteins, a sequence can contain amino acids that represent conservative amino acid substitutions, including but not limited to, the conservative substitution groups: Ser and Thr; Leu, Ile and Val; Glu and Asp; and Gln and Asn. A sequence as claimed herein thus includes the referenced sequence as well as its equivalents due to degeneracy in the genetic code. Conservative substitutions also can be determined by other methods, such as, without limitation, those used by the BLAST (Basic Local Alignment Search Tool) algorithm, the BLOSUM Substitution Scoring Matrix, and the BLOSUM 62 matrix (see also, for example, Altschul et al., *Methods in Enzymology* 266:460-479 (1996)). Importantly, "equivalents" and "conserved equivalents" of a reference nucleic acid or peptide/protein substantially retain or enhance the function of the reference nucleic acid or peptide/protein.

By the term "vector" is meant a means for introducing a foreign nucleotide sequence into a cell, including without limitation, a plasmid or virus. Such vectors can operate under the control of a host cell's gene expression machinery. A vector contains sequences that facilitate replication and/or maintenance of a segment of foreign nucleic acid in the host cell. Generally, the vector is introduced into a host cell for the replication and/or expression of the segment of foreign DNA or for delivery of the foreign DNA into the host genome. A typical plasmid vector contains: (i) an origin of replication, so that the vector can be maintained and/or replicated in a host cell; (ii) a selectable marker, such as an antibiotic resistance gene to select cells containing the vector (transformants) among vectorless cells, and (iii) a polylinker site containing several different restriction endonuclease recognition and cut sites to facilitate cloning of a foreign DNA sequence.

Provided herein are genes and genetic elements useful in modifying host cells. These host cells may include, for example, microorganisms. One particularly suitable microorganism for use in embodiments of the invention is the yeast *H. polymorpha* (*P. angusta*). Methods and compositions of the invention are useful for providing microorganisms with increased enzyme activity. In one embodiment, a *H. polymorpha* pyruvate decarboxylase is overexpressed.

A further embodiment provides a process for production of ethanol, including isolating from a donor yeast a first polynucleotide encoding a polypeptide including the amino acid sequence of SEQ ID NO: 1, or a fragment thereof, or an amino acid sequence at least 95% identical to SEQ ID NO: 1, wherein the polypeptide has pyruvate decarboxylase activity, constructing yeast vectors including the polynucleotide, transforming a host cell with the vectors obtained in step (b) to obtain a recombinant yeast strain; cultivating the recombinant yeast strain in a xylose-containing medium; and isolating and purifying ethanol formed in said medium. In another embodiment, the first polynucleotide has a sequence of SEQ ID NO: 3.

A further embodiment provides a process for production of ethanol, including isolating from a donor yeast of the species *K. lactis* a first polynucleotide encoding a polypeptide including the amino acid sequence of SEQ ID NO: 2, or a fragment thereof, or an amino acid sequence at least 95% identical to SEQ ID NO: 2, wherein the polypeptide has pyruvate decarboxylase activity, constructing yeast vectors including the polynucleotide, transforming a host cell with the vectors obtained in step (b) to obtain a recombinant yeast strain; cultivating the recombinant yeast strain in a xylose-containing medium; and isolating and purifying ethanol formed in said medium. In another embodiment, the first polynucleotide has a sequence of SEQ ID NO: 4.

In a further embodiment, the vectors further include a promoter operably associated with said first polynucleotide. In a yet still further embodiment, the promoter is selected from promoters of the GAP, PMA1, TEF1 genes. In a still further embodiment, the promoter is a *Hansenula polymorpha* glyceraldehyde-3-phosphate dehydrogenase promoter. The HpGAP promoter may have the nucleotide sequence of SEQ ID NO: 5.

In another embodiment of the invention, the vector further includes a terminator operably associated with the first polynucleotide. The terminator is selected, for example, from the group including terminators of the GAP, PMA1, TEF1 and AOX genes. In a preferred embodiment, the terminator is a *Hansenula polymorpha* alcohol oxidase promoter. The HpAOX promoter may have the nucleotide sequence of SEQ ID NO:6.

Another embodiment of the invention includes an isolated polynucleotide encoding a polypeptide including the amino acid sequence of SEQ ID NO: 1, or a fragment thereof, or an amino acid sequence at least 95% identical to SEQ ID NO: 1, wherein the polypeptide has pyruvate decarboxylase activity. A further embodiment of the invention includes an isolated polynucleotide encoding a polypeptide including the amino acid sequence of SEQ ID NO: 2, or a fragment thereof, or an amino acid sequence at least 95% identical to SEQ ID NO: 2, wherein the polypeptide has pyruvate decarboxylase activity.

The polynucleotide may include a promoter that controls expression of said polypeptide. The promoter may be, for example, selected from promoters of the GAP, PMA1, TEF1 genes. One useful promoter is a *Hansenula polymorpha* glyceraldehyde-3-phosphate dehydrogenase promoter. The HpGAP promoter may have the nucleotide sequence of SEQ ID NO: 5.

Polynucleotides of the invention may further include a terminator. The terminator may be selected, for example, from the group including terminators of the GAP, PMA1, TEF1 and AOX genes. In a preferred embodiment, the terminator is a *Hansenula polymorpha* alcohol oxidase promoter. The HpAOX terminator may have the polynucleotide sequence of SEQ ID NO:6.

Embodiments of the invention also include vectors and plasmids including polynucleotides of the invention. Embodiments of the invention further include one or more isolated host cells including plasmids that contain polynucleotides of the invention. The isolated host cell may be, for example, a strain of *Hansenula polymorpha*. Embodiments of the invention also include production of ethanol from a lignocellulosic starting material by culturing host cells of the invention in a medium including lignocellulosic starting material. Host cells of the invention may also be cultivated in a medium containing xylose but without other lignocellulosic materials.

In one embodiment, an isolated polynucleotide is provided, comprising a promoter operably associated with an open reading frame (ORF) and a terminator. In one embodiment, the promoter is the *H. polymorpha* GAP promoter (the promoter of the glyceraldehyde-3-phosphate dehydrogenase gene) (SEQ ID NO: 5), the ORF is the *H. polymorpha* PDC1 gene (SEQ ID NO: 3), and the terminator is the *H. polymorpha* AOX terminator (the terminator of the alcohol oxidase gene) (SEQ ID NO: 6).

In other embodiments, the promoter may be selected from promoters of the GAP, PMA1, TEF1 genes, the ORF is selected from the *H. polymorpha* PDC1 gene, polynucleotide fragments including the *H. polymorpha* PDC1 gene, and polynucleotides including nucleotide sequences at least 95% identical to the PDC1 gene that encode polypeptides that have pyruvate carboxylase activity in *H. polymorpha*.

In a further embodiment, the ORF is selected from the *K. lactis* PDC1 gene (SEQ ID NO: 4), nucleotide fragments including the *K. lactis* PDC1 gene, and polynucleotides including nucleotide sequences at least 95% identical to the *K. lactis* PDC1 gene that encode polypeptides that have pyruvate decarboxylase activity in *H. polymorpha*.

Polynucleotides of the invention may be contained within a vector and/or host cell. In particular, plasmids including polynucleotides of the invention are provided. Also provided are methods of integrating the polynucleotides into the genome of a host cell.

Another embodiment provides a method for fermentative production of ethanol from a starting material including xylose. Another embodiment provides a method for manipulating carbon flux in a yeast cell comprising culturing a yeast cell containing a polynucleotide of the invention and recovering ethanol from a culture medium.

Those skilled in the art will, with the benefit of this disclosure, recognize that further modifications may be made to host cells of the invention, which allow for further nutritional requirements altered production of ethanol and/or other chemicals.

Strains and Plasmids

Microbial strains and plasmids used in embodiments of the invention are provided in Table 1.

TABLE 1

|  | Description | Source |
|---|---|---|
| Strains | | |
| *H. polymorpha* CBS4732s leu2-2 | leu2, deficient in β-isopropylmalate dehydrogenase | Dr. K. Lahtchev, Sofia, Bulgaria |
| *H. polymorpha* Pdc 1-6, 1-8 (NRRL Y-50060 and NRRL Y-50062, respectively) | Leu⁺ derivatives of CBS4732s leu2-2 containing the genome-integrated recombinant HpPDC1 gene | This disclosure |
| *H. polymorpha* NCYC495 leu1-1 (ATCC MYA-335) | leu2, deficient in β-isopropylmalate dehydrogenase | ATCC, USA |
| *H. polymorpha* 495 2Eth⁻ leu1-1 | derivative of NCYC495 leu1-1 with impairment for utilization of ethanol as sole carbon and energy source | This disclosure |
| *H. polymorpha* 495 2Eth⁻ leu1-1(pPDC1) | Leu⁺ derivative of 495 2Eth⁻ leu1-1 containing the genome-integrated recombinant HpPDC1 gene | This disclosure |
| *K. lactis* CBS 2359 | wt strain | CBS collection, Netherlands |
| Plasmids | | |
| pPDC1 | | This disclosure |
| pKlPDC1 | | This disclosure |

Embodiments of the invention are taught and described in the following two examples. Examples are intended to guide those skilled in the art in the practice of this invention. They should not be construed to limit the scope of the invention, which is defined by the claims.

EXAMPLE 1

Media and Culture Conditions

Media and culture conditions used in experiments for embodiments of the invention are provided below. Yeasts are grown in synthetic yeast nitrogen-base (YNB) medium supplemented with xylose as sole carbon and energy source (2%) at 37° C. Liquid-medium cultivations were conducted in 40 ml of the medium with 12% xylose in 125-ml Erlenmeyer shake flasks at a shaker at 37 or 48° C. Oxygen-limited conditions were provided by agitating at 135-140 rpm. The starting cell density after inoculation is ~2 mg of dry weight× ml⁻¹. Media are inoculated from cultures pregrown in 80 ml of YPX medium (1% yeast extract, 2% peptone, 8% xylose) at cultivation in 300-ml flasks with shaking at 220 rpm until middle-exponential growth phase. Cells for inoculation are harvested by centrifugation, washed with water and concentrated to achieve the starting density mentioned above.

Those skilled in the art will recognize that other media may be used depending on the growth conditions desired and on the composition of the lignocellulosic material to be used as a raw material for the fermentation.

Enzymes, Primers, and Chemicals

A fragment containing the ORF of the HpPDC1 was isolated by PCR from genomic DNA of the strain CBS 4732s leu2-2 using primers K10 (CGC CATATGTCTGAATCCCAACTACC) (SEQ ID NO: 7) and K11 (TTTGCGGCCGCTTAAGCTGCATTGATCTGC) (SEQ ID NO: 8). Restriction sites Nde I and Not I were incorporated into the primers K10 and K11, respectively, to provide correct orientation of the isolated PCR fragment (the HpPDC1 ORF) into the corresponding site of the plasmid pKO8-GAPpr (description and linear scheme of the plasmid: see the article Voronovsky A. Y. et al., "Expression of xylA Genes Encoding Xylose Isomerases From *Escherichia coli* and *Streptomyces coelicolor* in the Methylotrophic Yeast *Hansenula polymorpha*" FEMS Yeast Res. 5(11): 1055-62 (2005)). Restriction enzymes, DNA modifying enzymes, and other reagents were obtained from New England Biolabs, USA, Sigma, USA and Fermentas, Lithuania.

A fragment containing the ORF of the KlPDC1 gene was isolated from genomic DNA of the *K. lactis* strain CBS 2359 using primers IS3 (GCG AAGCTTATGTCTGAAATTACATTAGG) (SEQ ID NO: 9) and IS4 (CATAAGCTTTTAGTTCTTAGCGTTGGTAG) (SEQ ID NO: 10). Restriction enzymes, DNA modifying enzymes, and other reagents were obtained from New England Biolabs, USA, Sigma, USA and Fermentas, Lithuania.

Reaction conditions employed were as recommended by the suppliers. Genomic DNA of *H. polymorpha* and *K. lactis* was isolated using the Wizard® Genomic DNA Purification Kit (Promega, USA). Restriction endonucleases and DNA ligase (Fermentas, Lithuania and New England Biolabs, USA) were used according to the manufacturer specifications. Plasmid isolation from *E. coli* was performed with the Wizard® Plus SV Minipreps DNA Purification System (Promega, USA). DNA fragments were separated on 0.8% agarose (Fisher Scientific, USA) gel in 1×TAE (Sambrook et al. Molecular Cloning: A Laboratory Manual. Cold Spring Harbor Laboratory, Cold Spring Harbor, N.Y. 1989.). Isolation of fragments from gel was carried out with the DNA Gel Extraction Kit (Millipore, USA). Amplification of PDC1 ORFs, HpGAP promoter and HpAOX terminator was done with Platinum® Taq DNA Polymerase High Fidelity (Invitrogen, USA) according to the manufacturer specification. PCRs were performed in GeneAmp® PCR System 9700 thermocycler (Applied Biosystems, USA). With the benefit of this disclosure, those skilled in the art will recognize that the transformations and isolations may be performed with any of a variety of known materials and methods.

Transformation

Those skilled in the art will recognize that a number of methods for transformation of *H. polymorpha* exist. For example, one may use the electroporation method reported in (Faber, K. N., et al., "Highly-efficient Electrotransformation of the Yeast *Hansenula polymorpha*" Curr. Genet. 25: 305-

310 (1994)). Transformation using intact cells may also be effective (Roggenkamp R. et al., "Transformation of the methylotrophic yeast *Hansenula polymorpha* by autonomous replication and integration vectors" *Mol Gen Genet.* 202: 302-308 (1986)).

Plasmid Construction

Recombinant plasmids carrying *H. polymorpha* PDC1 ORF (SEQ ID NO: 3) driven by the *H. polymorpha* GAP promoter (SEQ ID NO: 5) and terminated by the *H. polymorpha* AOX terminator (SEQ ID NO: 6), and also including the *Saccharomyces cerevisiae* LEU2 gene were constructed on the basis of the plasmid pKO8-GAPpr (Voronovsky A. Y. et al., "Expression of xylA Genes Encoding Xylose Isomerases From *Escherichia coli* and *Streptomyces coelicolor* in the Methylotrophic Yeast *Hansenula polymorpha*" *FEMS Yeast Res.* 5(11): 1055-62 (2005)). Construction of the plasmid pKO8-GAPpr is reported therein.

The plasmid pPDC1 (FIG. 6) was linearized by BamH I and used for transformation of *H. polymorpha* cells of the strain CBS 4732s leu2-2 and 495 2Eth⁻ leu1-1 to isolate Leu⁺ integrants containing the recombinant HpPDC1 ORF driven with the HpGAP promoter and terminated with the HpAOX terminator.

Figure 7:
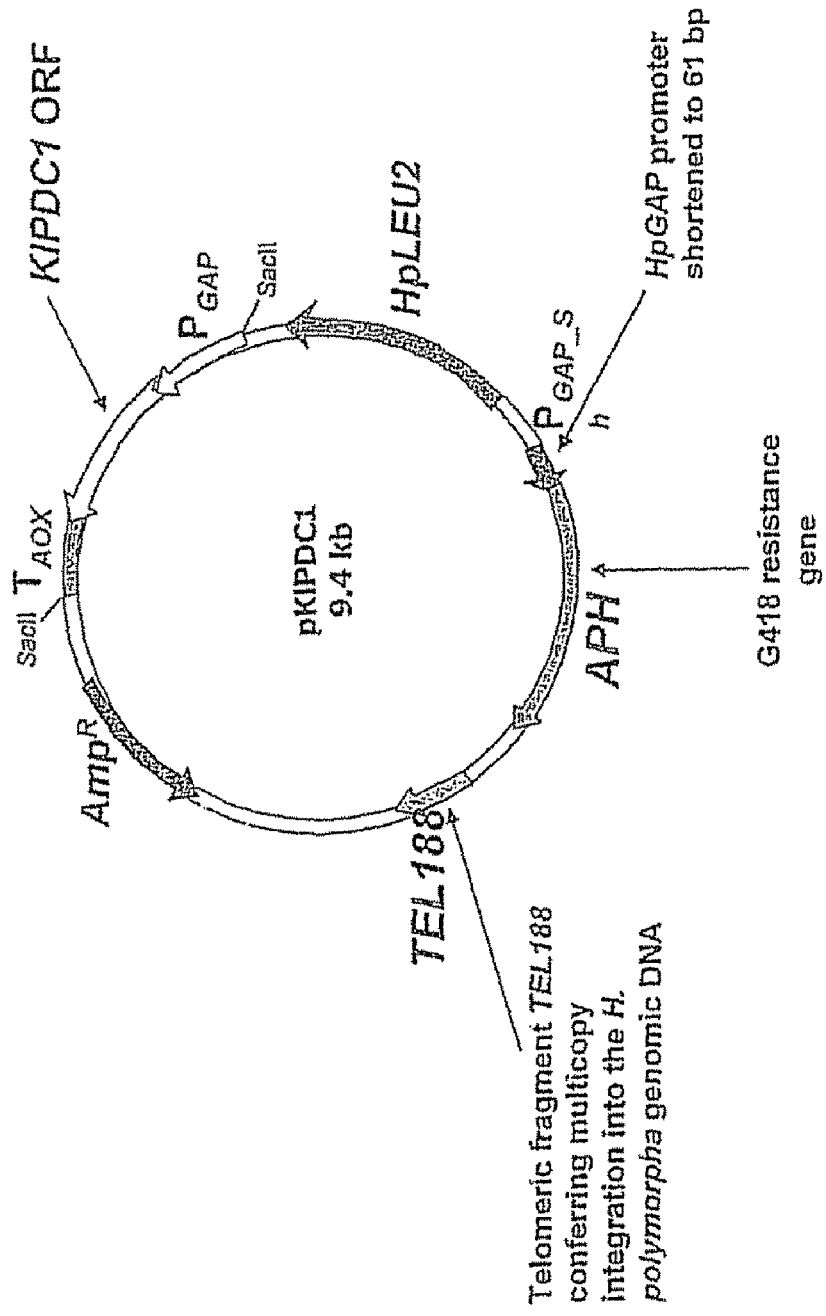
FIG. 7 shows a map of the plasmid pGLG_K1PDC1 containing the *Kluyveromyces lactis* PDC1 gene.
Figure 8:
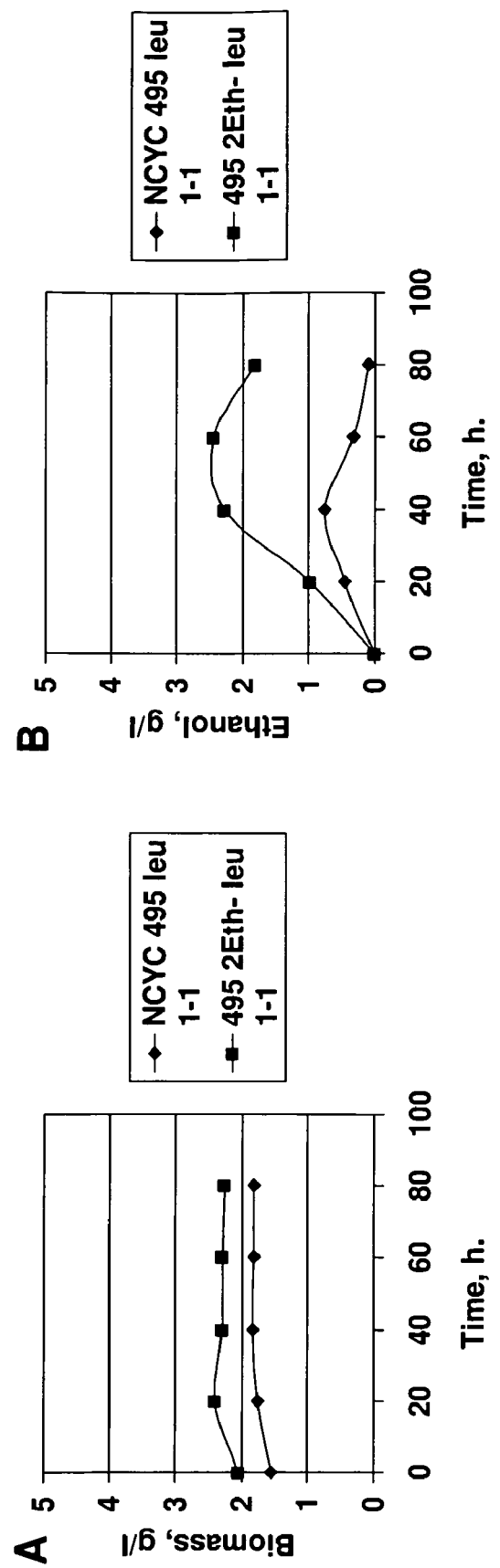
FIG. 8 shows an ethanol production during fermentation of xylose by the *H. polymorpha* strain NCYC 495 leu1-1 and its derivative 495 2Eth⁻leu1-1 at 48° C.

The recombinant plasmid pK1PDC1 (FIG. 7) carrying *K. lactis* PDC1 ORF (SEQ ID NO: 4) driven by the *H. polymorpha* GAP promoter (SEQ ID NO: 5) and terminated by the *H. polymorpha* AOX terminator (SEQ ID NO: 6), and also including the recombinant *Escherichia coli* kan$^r$ gene conferring G418 resistance were constructed on the basis of the plasmid pGLG61 (Gellissen G. (Ed). *Hansenula polymorpha*: Biology and Applications. Wiley-VCH, Weinheim. 365 p. 2002.).

Ethanol Assay

The "Alcotest" kit (Gonchar, M. V., Maidan, M. M., Sibirny, A. A. "A new oxidase-peroxidase kit 'Alcotest' for ethanol assays in alcoholic beverages" Food Technol Biotechnol. 39: 37-42 (2001)) was used for ethanol assays.

Trial 1

Trial 1 shows production of *H. polymorpha* transformants carrying the integrated recombinant HpPDC1. The *H. polymorpha* PDC1 gene (HpPDC1) (SEQ ID NO:3) encodes pyruvate decarboxylase. A 1.716 kb fragment (SEQ ID NO:3) (FIG. 2) containing the ORF of HpPDC1 was isolated by PCR from the genomic DNA of the strain CBS 4732s leu2-2 using primers K10 and K11.

Resulting PCR product (the ORF of HpPDC1) was treated with restriction endonucleases Nde I and Not I flanking the product. The Nde I-Not I-PCR product was ligated with the NdeI-NotI-linearized plasmid pKO8-GAPpr. It resulted in the construct pPDC1 (FIG. 6). The construct contains the ORF of HpPDC1 driven with the *H. polymorpha* GAP promoter (SEQ ID NO:5) and terminated with the HpAOX terminator (SEQ ID NO:6). In addition, pPDC1 contains the *Saccharomyces cerevisiae* LEU2 gene (ScLEU2). Recombinant plasmid pPDC1 harboring this construct is shown in FIG. 6.

The plasmid pPDC1 was used for the transformation of the *H. polymorpha* strains CBS 4732s leu2-2 and 495 2Eth⁻ leu1-1 by electroporation. Integrants containing both ScLEU2 and the recombinant HpPDC1 gene were selected among resulting Leu⁺ transformants. It was done by PCR using genomic DNA of the transformants as a template and corresponding primers for recombinant

```
HpPDC1
                                             (SEQ ID NO: 11)
(IS5: GCGGGCGCCCCAATTATCATTAATAATCACTC
and (SEQ ID NO: 12))
IS6: TAAGGCGCCAGCATCTTGACAATCAGCAG
and ScLEU2
                                             (SEQ ID NO: 13)
(IS25: CGGCTGCAGGAGAACTTCTAGTATATCTACATAC
and (SEQ ID NO: 14))
IS26: TATCTGCAGCTACGTCGTTAAGGCCGTTTCTG.
```

The recombinants Pdc 1-6, Pdc 1-8 and 495 2Eth⁻ leu1-1/pPDC1 ## 4, 5 and 10 were isolated as a result of the work.

Samples of recombinants isolated as a result of this example, as well as a host cell bearing the plasmid pKIPDC1, were deposited under the terms of the Budapest Treaty on Sep. 13, 2007, with the NRRL ARS Culture Collection located at 1815 North University Street, Peoria, Ill., United States of America. Each strain is listed below next to its assigned deposit number:

| | |
|---|---|
| CBS4732 leu2-2/pPDC1, Pdc 1-6 | NRRL Y-50060 |
| CBS4732 leu2-2/pPDC1, Pdc 1-8 | NRRL Y-50062 |
| 495 2Eth-leu 1-1/pPDC1 #4 | NRRL Y-50063 |
| 495 2Eth-leu 1-1/pPDC1 #5 | NRRL Y-50064 |
| 495 2Eth-leu 1-1/pPDC1 #10 | NRRL Y-50065 |
| 495 leu 1-1/pKIPDC1 | NRRL Y-50066 |

Trial 2

Trial 2 reports tests of pyruvate decarboxylase activity and ethanol production in *H. polymorpha* transformants produced in Trial 1. The transformants were grown in YNB medium with 12% xylose as carbon source with restricted aeration (140 rpm) at 37° C. Table 2 includes a comparison of pyruvate decarboxylase activity of the transformants compared to that of CBS 4732s leu2-2. Table 3 includes a comparison of the ethanol production of the transformants compared to that of CBS 4732s leu2-2.

TABLE 2

Pyruvate decarboxylase activity of the *H. polymorpha* transformants Pdc 1-6 and Pdc 1-8 possessing an integrated recombinant HpPDC1 gene.

| | CBS 4732s leu2-2 (control) | Pdc 1-6 | Pdc 1-8 |
|---|---|---|---|
| Activity, U/mg of protein | 0.23 | 0.732 | 0.889 |

TABLE 3

Ethanol production (mg/ml) with the *H. polymorpha* transformants Pdc 1-6 and Pdc 1-8 carrying the integrated recombinant HpPDC1 gene; YNB medium, 12% xylose; 37° C.

| Day | CBS4732s leu2-2 (control) | Pdc 1-6 | Pdc 1-8 |
|---|---|---|---|
| 1 | 0.722 | 0.833 | 0.833 |
| 2 | 0.916 | 1 | 1.198 |
| 3 | 1.265 | — | 1.487 |
| 5 | 1.529 | 2.03 | 1.735 |

Pyruvate decarboxylase activity was assayed according to Gounaris A. D. et al., "Pyruvate decarboxylase. I. Protein dissociation into subunits under conditions in which thiamine pyrophosphate is released." J Biol Chem. 246:1302-1309. (1971). "Alcotest" kit (Gonchar, M. V., Maidan, M. M., Sibirny, A. A. "A new oxidase-peroxidase kit "Alcotest" for ethanol assays in alcoholic beverages". Food Technol Biotechnol. 39: 37-42 (2001)) was used for ethanol assays. Fermentation was conducted in 40 ml of YNB medium with 12% xylose in 125-ml Erlenmeyer shake flasks at a shaker at 37° C. Oxygen-limited conditions were provided by agitating at 135-140 rpm. The starting cell density after inoculation was ~2 mg of dry weight×ml$^{-1}$. Media were inoculated with suspensions from pregrown cultures prepared as described in "Media and Culture Conditions" above.

Trial 3

Figure 9A:
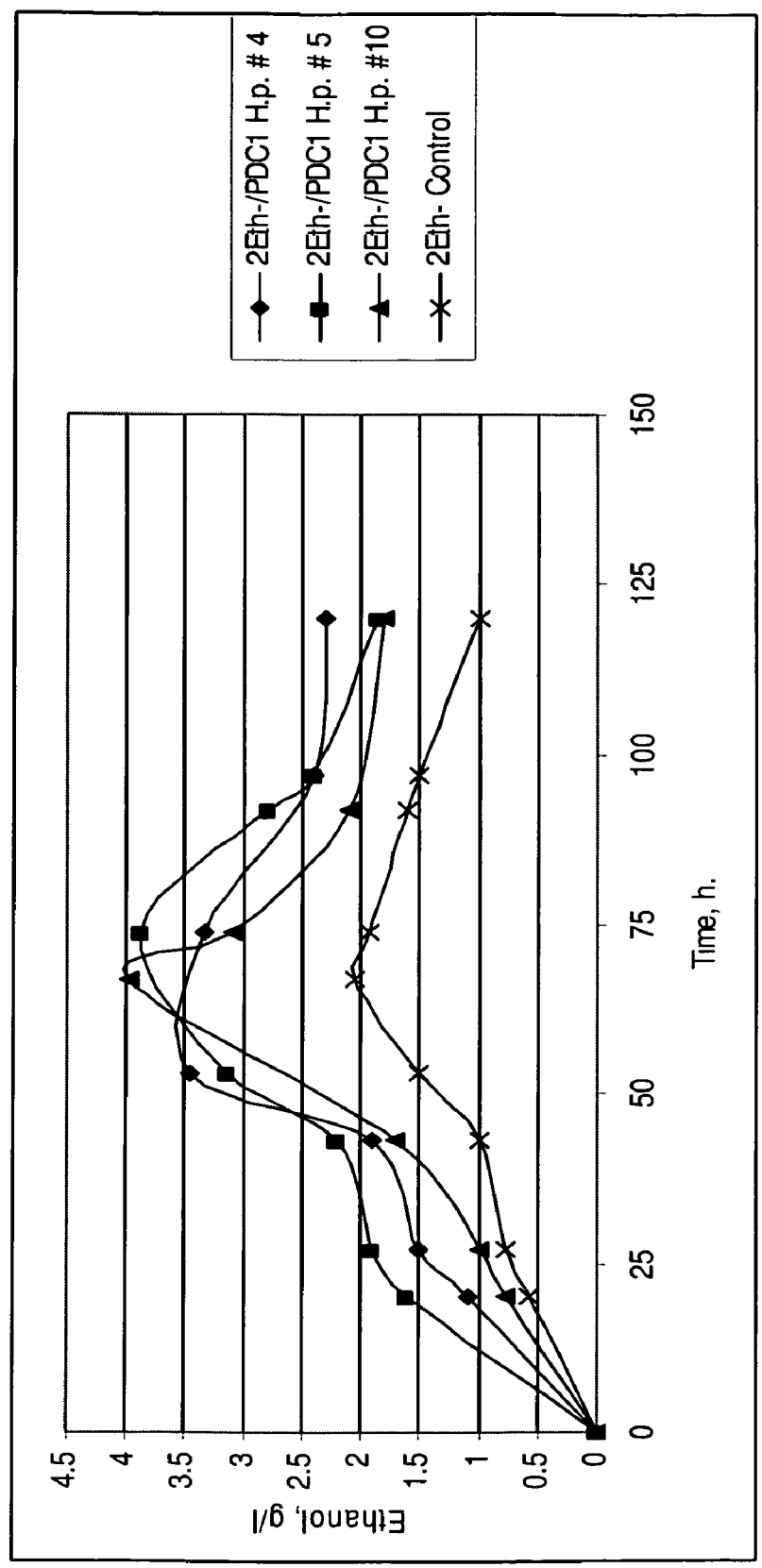
FIGS. 9a and 9b show an ethanol production during fermentation of xylose by the *H. polymorpha* transformants 495 2Eth⁻leu1-1/pPDC1 at 48° C.
Figure 9:
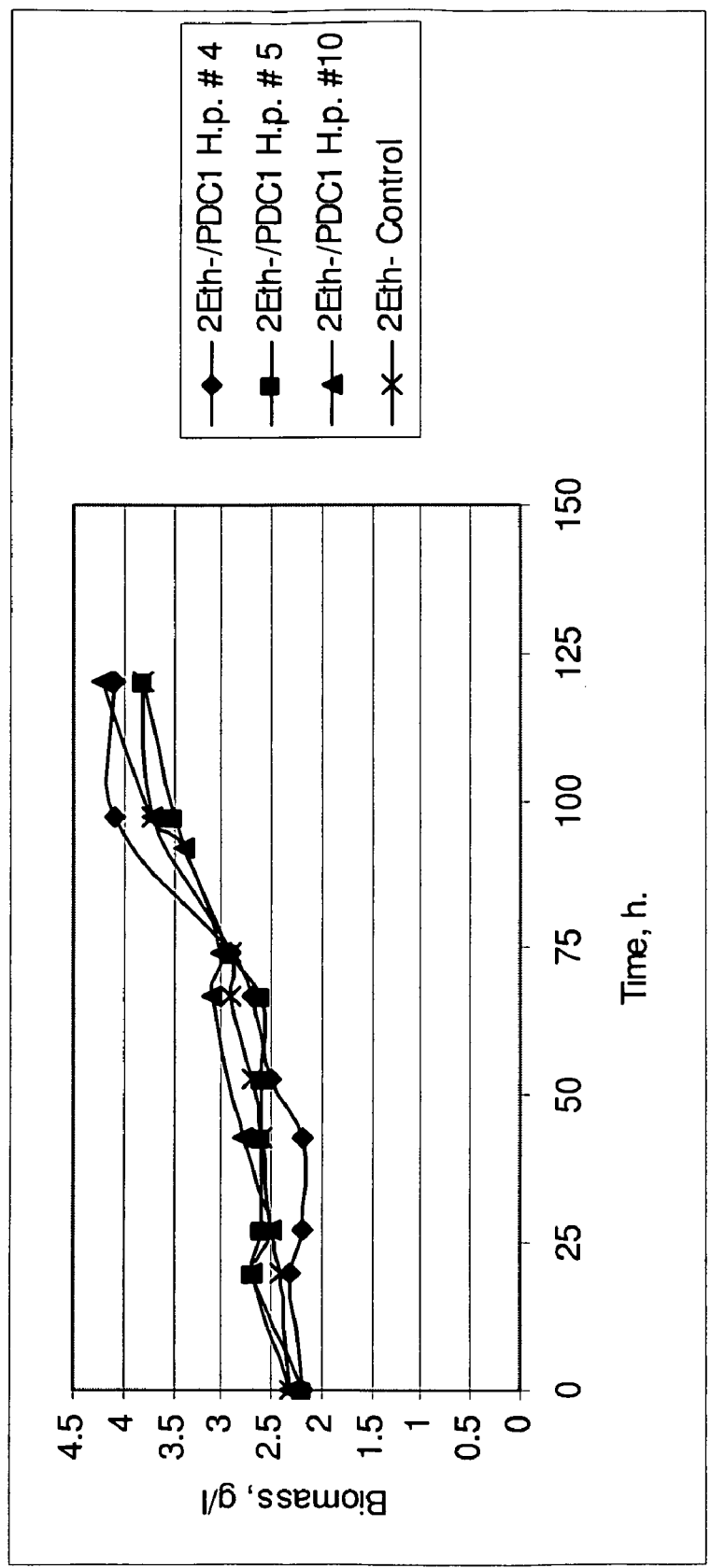

Trial 3 reports tests of ethanol production in *H. polymorpha* transformants produced in Trial 1. The transformants were grown in liquid YNB medium with 12% xylose as carbon source with restricted aeration (140 rpm) at 48° C. FIG. 9 includes a comparison of the ethanol production of the transformants compared to that of strain 495 2Eth$^-$ leu1-1.

EXAMPLE 2

Strains and Growth Conditions

Yeast strains *H. polymorpha* NCYC495 leu1-1 and 2EthOH— were used in this study as recipient strains for PDC1 gene overexpression. 2EthOH— is the UV-induced mutant derived from the parental strain NCYC495 leu1-1, which is unable to utilize ethanol as a carbon source and exhibits improved ethanolic fermentation of xylose.

Both NCYC495 leu1-1 and 2EthOH— are leu2 mutants that were maintained on minimal medium containing 0.67% YNB (Difco, Detroit, Mich., USA) supplemented with 2% sucrose and leucine at 40 mgxL$^{-1}$.

3Leu+ strain was used as a control strain. It is Leu+ transformant of NCYC495 leu1-1 with the plasmid pKO8-GAPpr (Voronovsky et al., 2005).

*H. polymorpha* CBS4732 was used as a source of PDC1 gene. This strain was kindly provided by Dr Lahtchev K (Institute of Microbiology, Bulgarian Academy of Sciences, Sofia, Bulgaria) and was maintained on YPD medium 0.5% yeast extract, 1% peptone and 2% glucose).

*Kluyveromyces lactis* CBS 2359 which was used a source of PDC1 gene was maintained on YPD.

Yeast transformants were selected either on YNB medium with 2% sucrose or on YPS medium (0.5% yeast extract, 1% peptone and 2% sucrose) supplemented with geneticin at 1 g×L- or zeocin at 140 mgxL$^{-1}$.

*Escherichia coli* strain DH5α (Φ80dlacZΔM15, recA1, enlA1, gyrA96, thi-1, hsdR17 ($r_K^-$, $m_K^+$), supE44, relA1, deoR, Δ(lacZYA-argF) U169) was used in experiments which required a bacterial host. The bacterial strain was grown at 37° C. in the rich (LB) medium as described in Sambrook et al., 1989. Transformed *E. coli* cells were maintained on a medium containing 100 mg×L$^{-1}$ of ampicillin or erythromycin.

Molecular Biology Techniques

Plasmid DNA isolations from *E. coli* were carried out by using NucleoSpin® Plasmid QuickPure (Macherey-Nagel, Germany). Taq DNA polymerase and Vent$_R$® DNA polymerase (both New England Biolabs, USA) were used for analytical and preparative PCR, respectively. T4 DNA ligase, T4 DNA polymerase and restriction enzymes were purchased from Fermentas, Lithuania.

Preparations of total DNA from yeast species were carried out by using DNeasy® Tissue Kit (Qiagen, Germany).

Transformation of *H. polymorpha* was performed by electroporation as described previously (Faber et al., 1994).

Southern blotting analysis was performed using the Amersham ECL Direct Nucleic Acid Labeling and Detection System (GE Healthcare, USA).

Cloning of the PDC1 Gene of *H. polymorpha*

As the complete sequence of *H. polymorpha* ORF of PDC1 gene is not available and there is just 949 bp internal part of the gene in the genome database "Genolevures" for *Pichia angusta/H. polymorpha* (NCBI accession number AL433358) the corresponding ORF was cloned. For this purpose there was decided to use the inverse PCR approach. The primers pairs were designed to amplify the regions flanking the 949 bp sequence of PDC1 ORF: K1 (5'-TGGTC-CTCGCTGAAGGCCGACTTGC-3') (SEQ ID NO: 15) and K2 (5'-GCGGTGTGTACATCGGAGTTCTGTCG-3') (SEQ ID NO: 16); K3 (5'-GTCGCCGACACCAAAGGTGGT-CAC-3') (SEQ ID NO: 17) and K4 (5'-GCCAT-TGCGGGCATGATGGCCGAG-3') (SEQ ID NO: 18).

A range of restriction endonucleases was used to choose the appropriate ones, which are located not far from the PDC1 ORF and present on the 949 bp sequence. Genomic DNA of *H. polymorpha* CBS4732 strain was digested with each of these restriction endonucleases, selfligated and resulting DNA samples were used as templates for PCR with the inverse primers: K1/K2 and K3/K4. The ~3.9 kb fragment was obtained in the inverse PCR (primers K3/K4) where the sample of *H. polymorpha* genomic DNA digested with SalI was used as a template. The ~3.4 kb fragment was obtained in the inverse PCR (primers K1/K2) where the sample of *H. polymorpha* genomic DNA digested with SacI was used as a template. Obtained PCR fragments were cloned into the multiple cloning site of the plasmid pUC19 and sequenced. Using nucleotide blast with yeasts sequences available the *H. polymorpha* ORF of PDC1 was detected.

Construction of Plasmids

The recombinant plasmid pKO8+prGAP+PDC1Hp (FIG. 10a) was constructed on the basis of plasmid pKO8-GAPpr (Voronovsky A Y, Ryabova O B, Verba O V, Ishchuk O P, Dmytruk K V & Sibirny A A (2005) Expression of xylA genes encoding xylose isomerases from *Escherichia coli* and *Streptomyces coelicolor* in the methylotrophic yeast *Hansenula polymorpha*. FEMS Yeast Res 5(11): 1055-1062). The genomic DNA of strain *H. polymorpha* CBS4732 served as a template to isolate the ORF of PDC1 gene with primers K10 (5'-CGCCATATGTCTGAATCCCAACTACC-3') (SEQ ID NO: 7) and K11 (5'-TTT GCGGCCGCTTAAGCTGCATTGATCTGC-3') (SEQ ID NO: 8). The PCR fragment was cut with NdeI and NotI at the underlined restriction sites and cloned into the NdeI/NotI-linearized pKO8-GAPpr.

The pGLG61+prGAP+PDC1Hp (FIG. 10b) was constructed on the basis of pGLG61 (Sohn et al., 1999) that was kindly provided by Dr Kang H A (Korea Research Institute of Bioscience and Biotechnology, Taejon, Korea). The plasmid pKO8+prGAP+PDC1Hp (FIG. 10a) served as a template to isolate the fragment carrying promoter GAPDH-ORF PDC1-terminator AOX with primers IS5 (5'-GCG GGCGCCCCAATTATCATTAATAATCACTC-3') (SEQ ID NO: 11) and IS6 (5'-TAA GGCGCCAGCATCTTGACAATCAGCAG-3') (SEQ ID NO: 12).

The PCR fragment was cut with NarI at the underlined restriction sites and cloned into the plasmid pGLG61.

The ploxZeoloxPDC1Hp (FIG. 10c) was constructed on the basis of pGLG61+prGAP+PDC1Hp (FIG. 10b). pGLG61+prGAP+PDC1Hp was cut with PstI and 7.56 kb fragment was ligated with 1.1 kb fragment containing zeocin resistance gene Zeo[r] amplified from the plasmid pPICZ-B (Invitrogen, Carlsbad, Calif., USA) with primers Ko58 (5'-CGGGGTACCTGCAGATAACTTCGTATAGCATAC-3') (SEQ ID NO: 19) and Ko59 (5'-CGGGGTAC CTGCAGTAATTCGCTTCGGATAAC-3') (SEQ ID NO: 20) and cut with PstI at the underlined restriction sites.

The p19L2+prGAP+PDC1Kl (FIG. 10d) was constructed on the basis of p19L2 (Voronovsky A, Abbas C A, Fayura L R, Kshanovska B V, Dmytruk K V, Sybirna K A & Sibirny A A (2002) Development of a transformation system for the flavinogenic yeast Candida famata. FEMS Yeast Res 2: 381-388). The expression cassette containing H. polymorpha promoter GAPDH and terminator AOX was isolated from the pKO8-GAPpr (Voronovsky et al., 2005) with restriction enzymes BamHI and SacI and ligated with BamHI/SacI-digested p19L2. The resulting plasmids was cut with HindIII and ligated with HindIII-digested PCR fragment carrying K. lactis ORF of PDC1 gene (it was amplified from the genomic DNA of K. lactis CBS 2359 using primers pair: IS3 5'-GC-GAAGCTTATGTCTGAAATTACATTAGG-3'(SEQ ID NO: 9) and IS4 5'-CATAAGCCTTTAGTTCTTAGCGTTGG-TAG-3(SEQ ID NO: 10)).

Ethanol Production Assay

Xylose fermentation and assay of ethanol concentration were carried out in 100 ml flasks containing 40 ml YNB media with 12% or 8% xylose. Yeast cells were inoculated to obtain the final density 2 mg×ml$^{-1}$ in the media and cultivated at 37° C. or 48° C. at conditions of restricted aeration (140 rpm) for 5 days. Samples of medium for ethanol production assay were taken each day. Concentration of ethanol in the medium was determined using the "Alcotest" kit.

Enzyme Assays

The pyruvate decarboxylase activity was measured according to the method described earlier (Postma E, Verduyn C, Scheffers W A & Van Dijken J P (1989) Enzymic analysis of the crabtree effect in glucose-limited chemostat cultures of Saccharomyces cerevisiae. Appl Environ Microbiol 55(2): 468-477). Alcohol dehydrogenase with ethanol as substrate was determined by the rate of NADH formation monitored spectrophotometrically at 340 nm. Samples for the enzyme assay measurements were taken from the cultures on the third day of fermentation. The enzyme activity was measured directly after the preparation of cell-free extracts.

Native PAGE Electrophoresis

Cell-free extracts isolated from xylose-grown cells of NCYC 495 (wild type) and of 2EthOH$^-$ mutant were used for native protein PAGE. To visualize enzyme bands in native PAGE, a modified mixture was used: 10 mM NAD, 0.1 mM nitrotetrazolium blue, 0.003 mM phenazine methosulfate in 50 mM K,Na-phosphate buffer, pH 7.5, with EthOH (up to 500 mM) for Eth-dehydrogenase assay, and Benzylaldehyde (up to 10 mM) with addition KCl (up to 100 mM) for unspecific aldehyde-dehydrogenase assay.

Protein Determination

Protein was determined by the Lowry method (Lowry O H, Rosebrough N J, Farr A L & Randall R J (1951) Protein measurement with the Folin phenol reagent. J Biol Chem 193(1): 265-275) with bovine serum albumin as a standard.

Reverse transcription-polymerase chain reaction (RT-PCR) analysis

Total RNA was extracted from yeast cells using Trizol method (Invitrogen, Carlsbad, Calif.) following the manufacturer's protocol. RNA was quantified by UV spectrophotometry and diluted in RNase-free water. Single stranded cDNA was synthesized using MuLV reverse transcriptase (First Strand cDNA Synthesis Kit, Fermentas). Quantitative RT-PCR analysis was carried out using gene specific primer pairs and cDNA as a template: Primers pairs used: IS271 (5'-TG-GTCTTGCGGCTGCTCTGTTCACC-3') (SEQ ID NO: 21) and IS272 (5'-GTAAAGATCAAGGGCGTAGGTGC-CCAG-3') (SEQ ID NO: 22) for 3'-fragment of H. polymorpha ORF116 (Hp_contig12); IS273 (5'-GTCTTCTCCAAG-GATTTCCATAGAGCACATC-3') (SEQ ID NO: 23) and IS274 (5'-GCCAATGTTCAAGTAGATGCTCTTTGACTG-3') (SEQ ID NO: 24) for 3'-fragment of H. polymorpha ORF168 (Hp_contig15); IS275 (5'-CTACGTCTCCGACA-GACTCGAGGC-3') (SEQ ID NO: 25) and IS276 (5'-ACAGCCTTGACCTGGGTGTAGCTCTC-3') (SEQ ID NO: 26) for 3'-fragment of H. polymorpha ORF226 (Hp_contig01); IS277 (5'-GACACCGCCACCTACGTCTCCAAC-3') (SEQ ID NO: 27) and IS278 (5'-ACCAATTCTCACAGC-CTTCCACTGGGTG-3') (SEQ ID NO: 28) for 3'-fragment of H. polymorpha ORF313 (Hp_contig08); IS279 (5'-GC-CTACCTGTTCACTCAAGACATCAATCGG-3') (SEQ ID NO: 29) and IS280 (5'-GCTGAATGCTGCCAAGCCG-GCTTC-3') (SEQ ID NO: 30) for 3'-fragment of H. polymorpha ORF529 (Hp_contig47); ACT1F (5'-TGTCGTC-CCAGTTGGTAACG-3') (SEQ ID NO: 31) and ACT1R (5'-GGCCCAATCCAAGAGAGGTAT-3') (SEQ ID NO: 32) for 3'-fragment of H. polymorpha ORF of ACT1 gene (orf262, Hp_contig01).

High Temperature Xylose and Glucose Fermentation of Xylose in H. polymorpha

Figure 11:
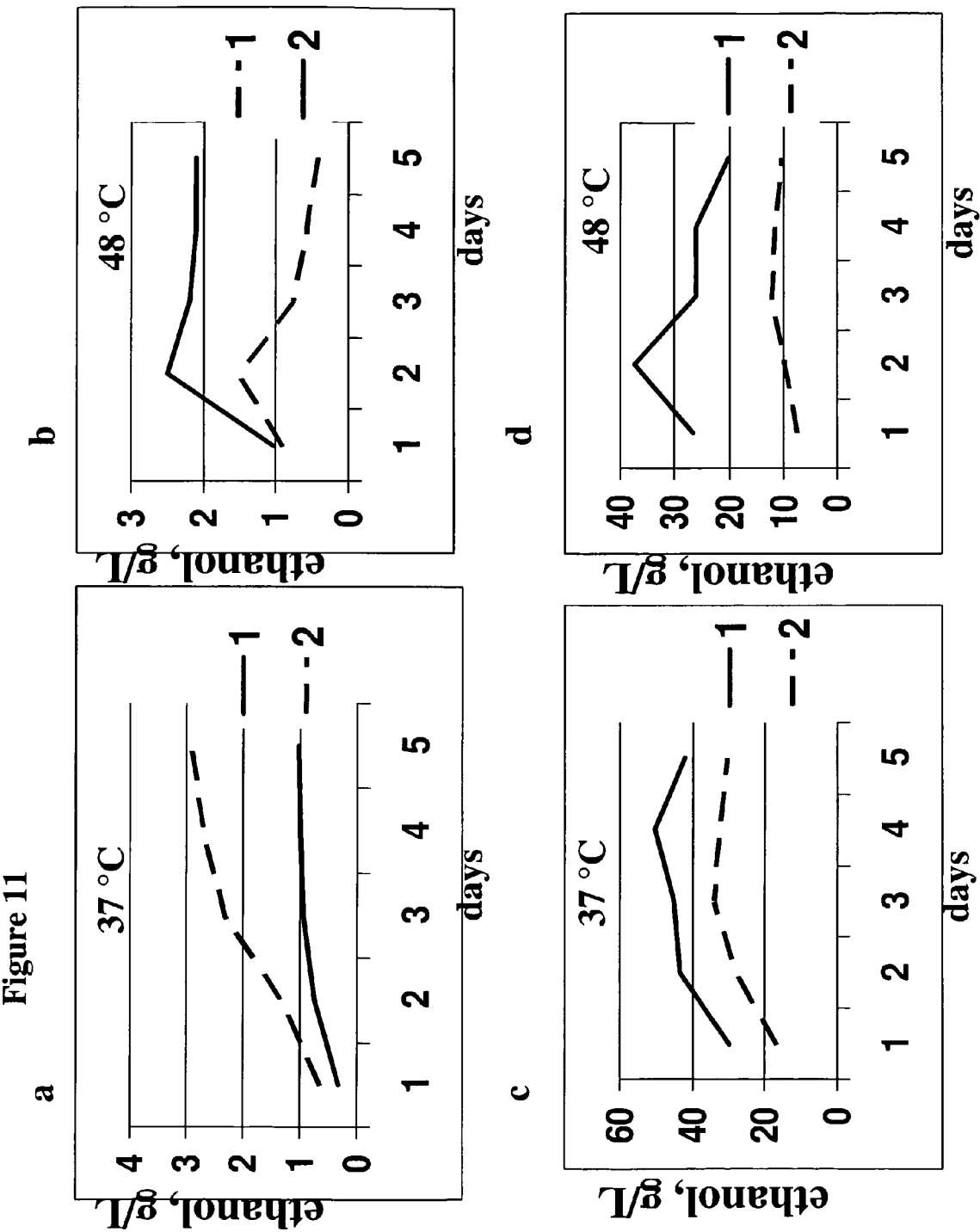
FIG. 11 shows the ethanol production of *H. polymorpha* strains during fermentation. a—xylose fermentation at 37° C. (YNB+12% xylose); b—xylose fermentation at 48° C. (YNB+12% xylose); c—glucose fermentation at 37° C. (YNB+12% xylose); d—glucose fermentation at 48° C. (YNB+12% xylose). Strains: 1—NCYC495 leu1-1, 2—2EthOH—.

In this Example, the glucose and xylose fermentation profiles of H. polymorpha NCYC495 leu$^{-1}$ were compared at the optimal growth temperature 37° C. and at the increased temperature of 48° C. An earlier study reported that the higher temperature of 48° C. induced heat-shock in this yeast. In this Example it is shown that ethanol accumulation profiles are similar for glucose and xylose at both 37° C. and 48° C., however, at high temperature ethanol, accumulated in first two days, disappeared during further incubation (FIG. 11). Such disappearance could occur due to reutilization of accumulated ethanol.

To test this hypothesis, we decided to isolate mutant of H. polymorpha unable to utilize ethanol as sole carbon and energy source and to compare fermentation of xylose and glucose fermentation of parental and mutant strains. For this, parental strain NCYC495 leu1-1 was UV-mutagenized as described in Johnson et al., 1999, and resulting glucose-growing colonies were replica-plated on YNB medium supplemented with 1% (v/v) ethanol. Several clones were identified from appr. 10 thousand tested that are as unable to grow on 1% ethanol as a single carbon source. However, most of them still reutilized accumulated ethanol during xylose fermentation, though to lesser extent relative to parental strain NCYC 495 leu1-1.

One of isolated mutants designated as 2EthOH$^-$ utilized the least amounts of accumulated ethanol during xylose fermentation (FIG. 11) and therefore was studied in more details. It was also identified as a mutant clone, specifically unable to utilize ethanol, but simultaneously exhibiting the wild-type growth rate on the media supplemented with glucose, sucrose, glycerol or methanol. The 2EthOH$^-$ strain was further tested for ability to utilize ethanol catabolites, acetate and succinate, as carbon sources, and exhibited a wild-type growth rate on both of these substrates (not shown). Therefore, it was assumed that this mutant has a metabolic block in one of the two enzymatic stages of ethanol conversion to acetate, either alcohol dehydrogenase, acetaldehyde dehydrogenase, or both of these activities. To specify possible enzymatic defects leading to inability of mutant 2EthOH$^-$ to utilize ethanol and allowing utilization of acetate, activities of alcohol and aldehyde dehydrogenases were analyzed in cell-free extracts of strains NCYC 495 (wild type) and 2EthOH⁻. Cells were cultivated in xylose-containing medium at conditions used for monitoring alcoholic fermentation for three days. Extracts were loaded on PAGE and were used for native electrophoresis.

Figure 12:
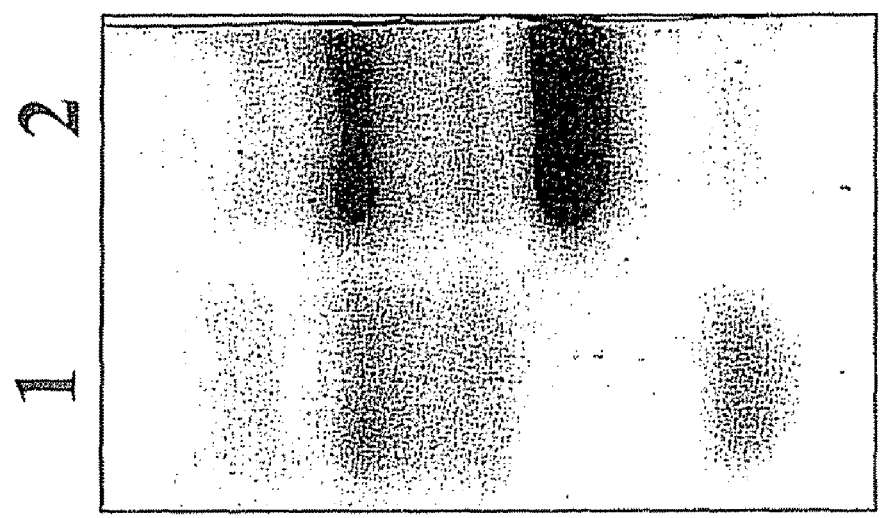
FIG. 12 shows the alcohol dehydrogenase activity of *H. polymorpha* strains visualized on native protein PAGE. Protein samples were taken from cell-free extracts of cells of the third day of xylose fermentation at 48° C. Lane 1, NCYC495; lane 2, 2EthOH—. 0.1 mg of protein was loaded to each lane. Total ADH activities were 0.035 U in NCYC495 and 0.2 U in 2EthOH—.
Figure 13:
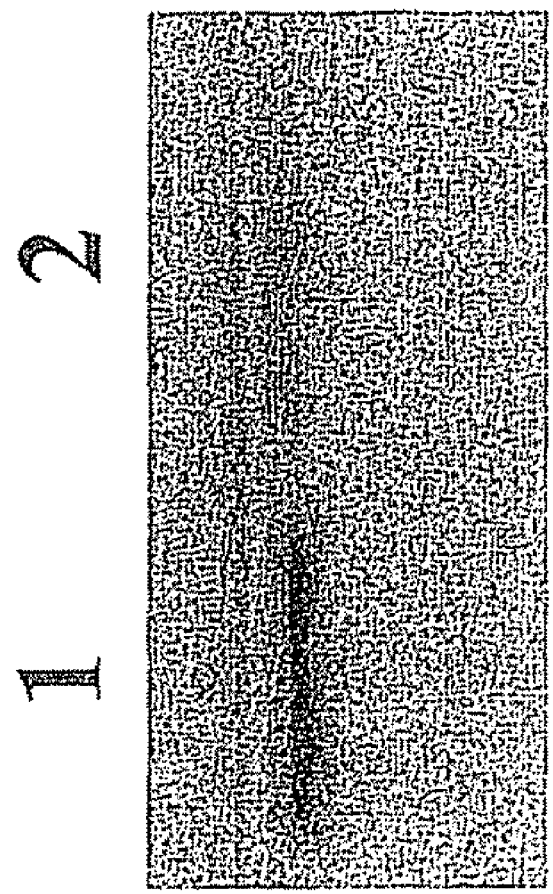
FIG. 13 shows the aldehyde dehydrogenase activity of *H. polymorpha* strains visualized on native protein PAGE. Protein samples were extracted with 0.1% Triton from disrupted cells debris of cells of the third day of xylose fermentation at 48° C. Lane 1, NCYC495; lane 2, 2EthOH—. 0.1 mg of protein was loaded to each lane.

It was found that mutant 2EthOH⁻ differs from wild-type strain by number of alcohol dehydrogenase bands, almost totally lacking two of them (FIG. 12). At the same time, two bands of alcohol dehydrogenase were much more profound relative to that in the wild-type strain. Aldehyde dehydrogenase activity was substantially lower in extract of the 2EthOH⁻ mutant relative to that of the wild-type strain (FIG. 13). It is interesting to note that one band of aldehyde dehydrogenase activities was totally absent in extracts of mutant 2EthOH— (FIG. 13). In S. cerevisiae acetate is mainly produced by the cytosolic Ald6p and by a mitochondrial route involving Ald5p. The H. polymorpha blast search against S. cerevisiae ALD6/ALD5 protein sequences revealed 5 ORF sequences (ORF 116, 168, 226, 313 and 529) showing 61-74% homology to query gene.

Analysis of the mRNA quantity of 5 aldehyde dehydrogenase genes of H. polymorpha by RT-PCR showed that the 2EthOH⁻ strain has decreased expression of 4 aldehyde dehydrogenase genes (ORF 116, 226, 313 and 529) comparing to the NCYC495 strain, 3Leu+ (FIG. 14). Though not wishing to be bound by theory, we suggest that it is impaired in some regulatory gene involved in regulation of enzymes of primary ethanol metabolism along with some other enzymes involved in xylose and glucose fermentation.

We found that the 2EthOH⁻ mutant has significantly reduced ability to consume accumulated ethanol (FIG. 11) and this can be explained by its inability to utilize this alcohol as a single carbon source. It was found that the 2EthOH⁻ strain exhibits much higher level of ethanol synthesis from xylose than that of NCYC495 leu1-1 during fermentation at 37/48° C., and yields approximately 3.0 fold higher ethanol concentration on the third day of fermentation (FIG. 11a, FIG. 11b). At the same time, the mutant 2EthOH— grows and ferments glucose more slowly relative to the wild-type strain NCYC 495 leu1-1 (FIG. 11c, FIG. 11d). The reasons of the observed phenomena are unknown. Apparently, mutation in 2EthOH— strain oppositely affects glucose and xylose fluxes to ethanol.

Overexpression of the PDC1 Gene in the H. polymorpha Wild-Type Strain and the mutant 2EthOH—

Figure 15:
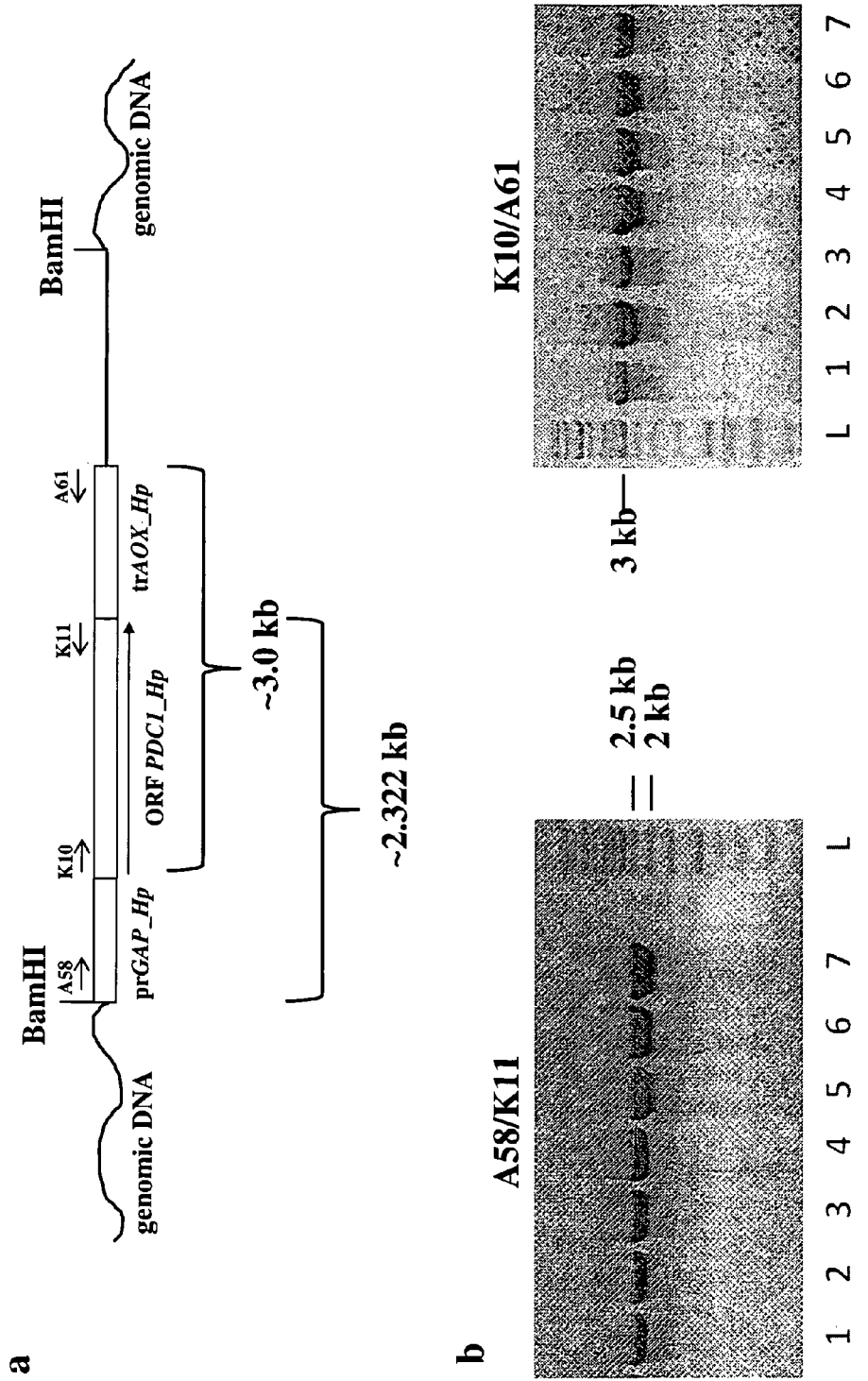
FIG. 15 shows the confirmation of the presence of PDC1 expression cassette in the genome of NCYC495 transformants by PCR. a—the schematic representation of the plasmid integrated into the genome, primers selected for checking are indicated (K10, K11, A58, A61); b—electrophoresis of PCR using primers pairs A58/K11 and K10/A61, line 1-7—stable transformants, L—DNA ladder.

One of the key aims of our study was to check the effect of pyruvate decarboxylase overexpression, a key enzyme in alcoholic fermentation, on xylose fermentation of H. polymorpha. The NCYC495 leu1-1 was used as the recipient strain. The plasmid pKO8+prGAP+PDC1Hp (FIG. 10a) was linearized and transformed into the NCYC495 leu1-1. The transformants were selected by leucine prototrophy on the YNB medium with 2% sucrose as a sole carbon source. The stability of these transformants was verified by the alternative cultivation in rich (YPD) and minimal (YNB with 2% sucrose) media. The transformants which remained prototrophs after such cultivation were identified and the presence of the desirable constructs in their genome (promoter GAPDH fused to ORF PDC1 with terminator AOX) was confirmed by PCR (FIG. 15a, FIG. 15b) (for this purpose the primers pair A58/K11 (for H. polymorpha promoter GAPDH primer A58 (5'-CGCGAGCTCCCAATTATCATTAATAATCAC-3') (SEQ ID NO: 33) and for ORF PDC1 primer K11); and also primers pair K10/A60 (K10 for ORF PDC1 and A61 (5'-TATCCGCGGAGCATCTTGACAATCAG-3') (SEQ ID NO: 34) for the terminator AOX) were used. The ethanol production from glucose, D-xylose, and L-arabinose and pyruvate decarboxylase activities were studied in the corresponding transformants in comparison to the control leucine prototrophic transformant, which carries the empty vector pKO8-GAPpr (Voronovsky et al., 2005).

Figure 16:
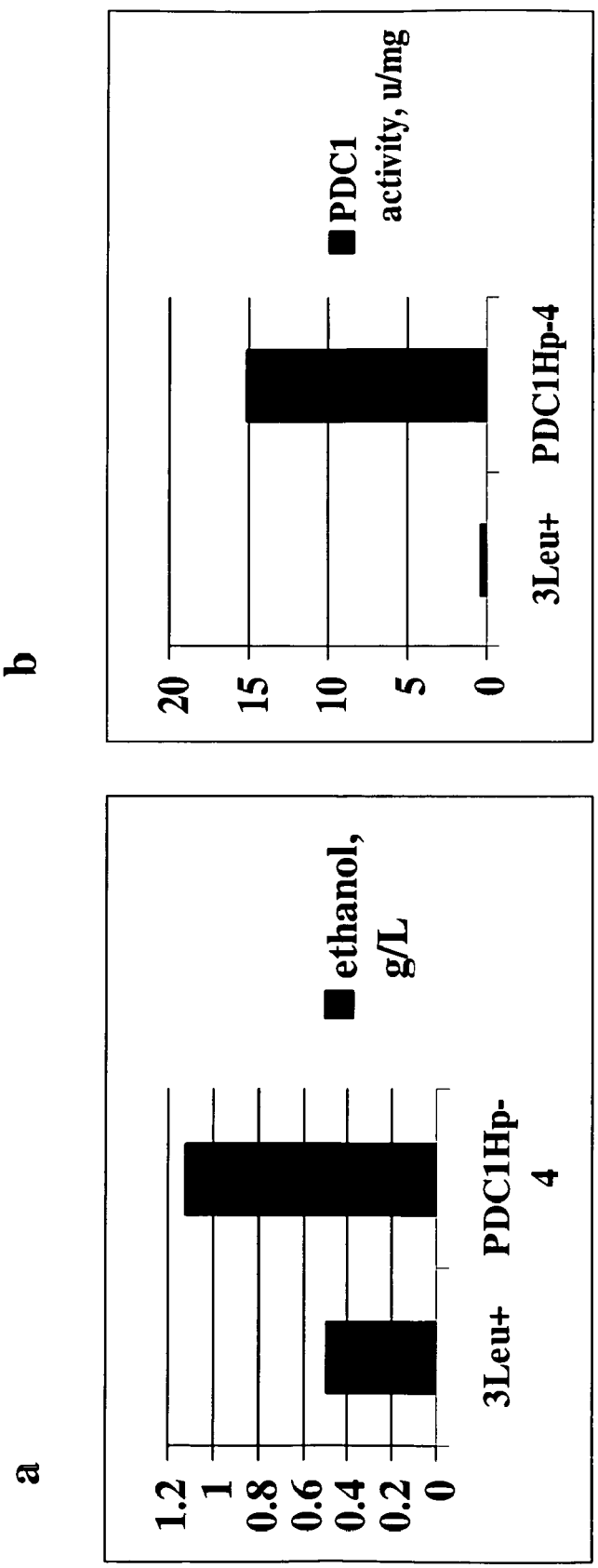
FIG. 16 shows the ethanol production (a) and specific activity of Pdc1(b) of *H. polymorpha* NCYC495 transformants. 3Leu+—control strain, Leu+ transformant, PDC1Hp-4—transformant carrying plasmid pKO8+prGAP+PDC1Hp. The samples for ethanol concentration estimation and pyruvate decarboxylase assay were taken from the third day of fermentation of xylose (YNB with 8% xylose, 37° C. and 140 rpm).

The overexpression of H. polymorpha PDC1 gene under control of H. polymorpha GAPDH (GAP is used as the name in all publications) promoter in all transformants resulted in the increased pyruvate decarboxylase activity and showed positive effect on fermentation of both glucose and xylose. In one of the transformants, PDC1Hp-4 the pyruvate decarboxylase activity was 40.9 fold higher relative to that of the parental strain (FIG. 16b), and this increase was accompanied by the 2.3 fold higher ethanol yield from xylose (FIG. 16a). On the medium with L-arabinose, transformants were characterized by better growth, however no ethanol was accumulated on this pentose, similarly to the parental strain (Table 2).

As the expression of PDC1 in NCYC495 was successful, we decided to use the same approach in 2EthOH⁻ strain which is the better ethanol producer from xylose relative to NCYC495 (FIG. 11). In case of 2EthOH⁻ transformation, the plasmids promoting multi-copy integration were used: pGLG61+prGAP+PDC1Hp and ploxZeoloxPDC1Hp (FIG. 10b, FIG. 10c). The pGLG61+prGAP+PDC1Hp is a derivative of pGLG61, and due to the presence of the telomeric autonomous replication sequence and the bacterial aminoglycoside 3-phosphotransferase (APH, zeocin resistance) gene, this vector promotes copy-number-controlled integration of plasmid tandem repeats into the genome. In addition, the vector ploxZeoloxPDC1Hp contains the Zeo$^r$ gene flanked by loxP sequences which provides for the efficient excision of this marker gene after integration (loxP/Cre), and the possibility to transform again with the same marker after its selective rescuing.

2EthOH⁻ transformants with pGLG61+prGAP+PDC1Hp were selected on YPS medium supplemented with 1 g×L⁻¹ of geneticin, G418. 2EthOH⁻ transformants with ploxZeoloxPDC1Hp were selected on YPS medium supplemented with 140 mg×L⁻¹ of zeocin. The stability of corresponding transformants was checked by the alternative cultivation in rich (YPS) and selective medium YPS with geneticin/zeocin. The presence of desirable recombinant constructs (promoter GAPDH fused to ORF PDC1 with terminator AOX) in the genome of stable transformants was confirmed by PCR.

Figure 10:
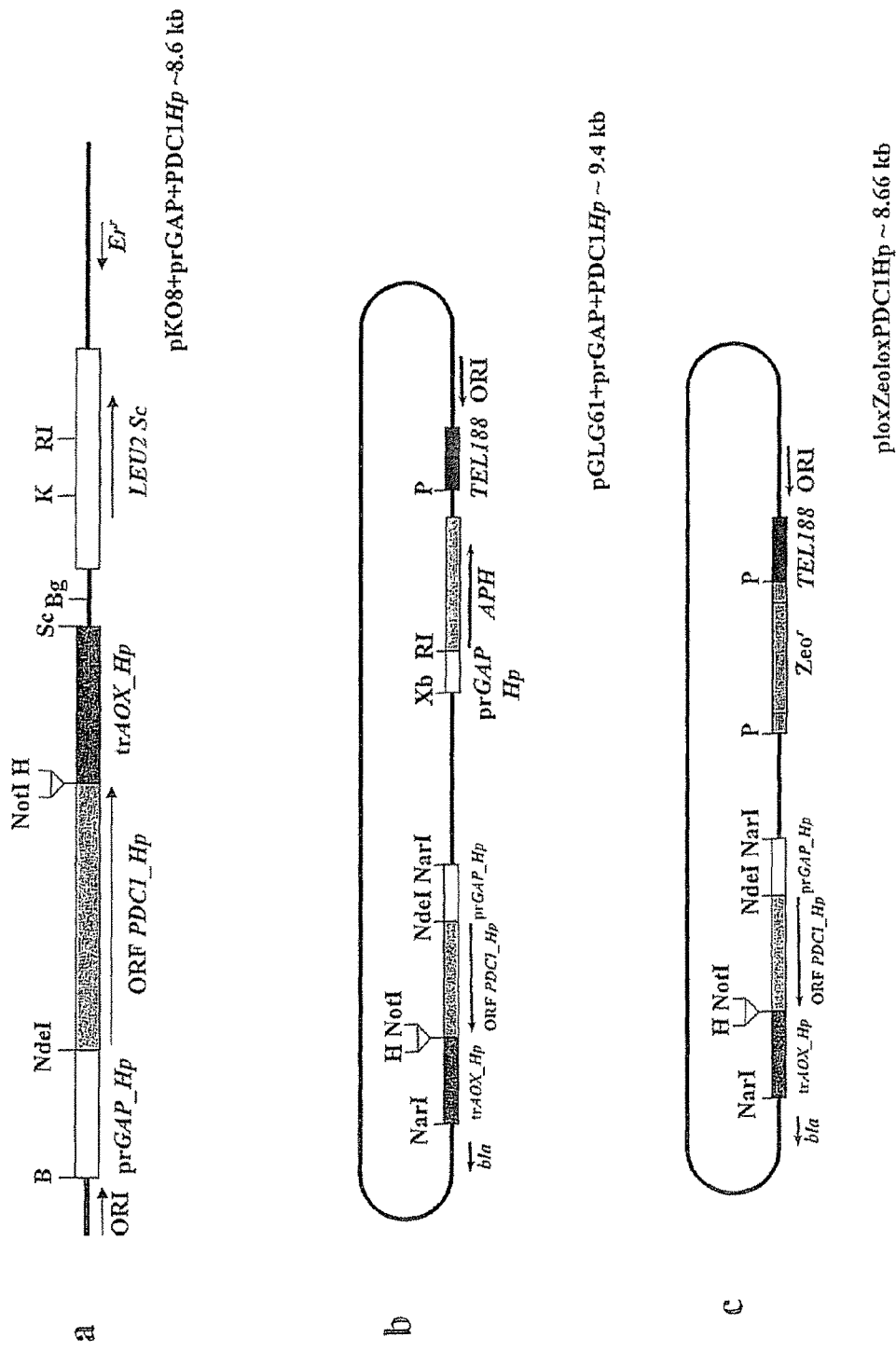
FIG. 10 shows the linear schemes of the plasmids pKO8+prGAP+PDC1Hp, pGLG61+prGAP+PDC1Hp, ploxZeoloxPDC1Hp and p19L2+prGAP+PDC1K1. Features include *H. polymorpha* PDC1 ORF (ORF PDC1_H1), the *K. lactis* PDC1 ORF (ORF PDC1_K1), the promoter of glyceraldehydes-3-phosphate dehydrogenase (GAPDH) of *H. polymorpha* (pr GAP_Hp), the terminator of alcohol oxidase of *H. polymorpha* (trAOX_Hp), the LEU2 gene of *S. cerevisiae* (LEU2 S_c), the geneticin resistance gene (APH), the telomeric region (TEL188) (Sohn et al., 1999) as an autonomously replicating sequence (TEL188), the zeocin resistance gene (Zeo_r), and loxP sequences (flanking the zeocin resistance gene). Restriction sites: B, BamHI; H, HindIII; Sc, SacI; Bg, BglII; K, KpnI; RI, EcoRI; Xb, XbaI; P, PstI; SalI, SI; SphI, Sp.
Figure 10:
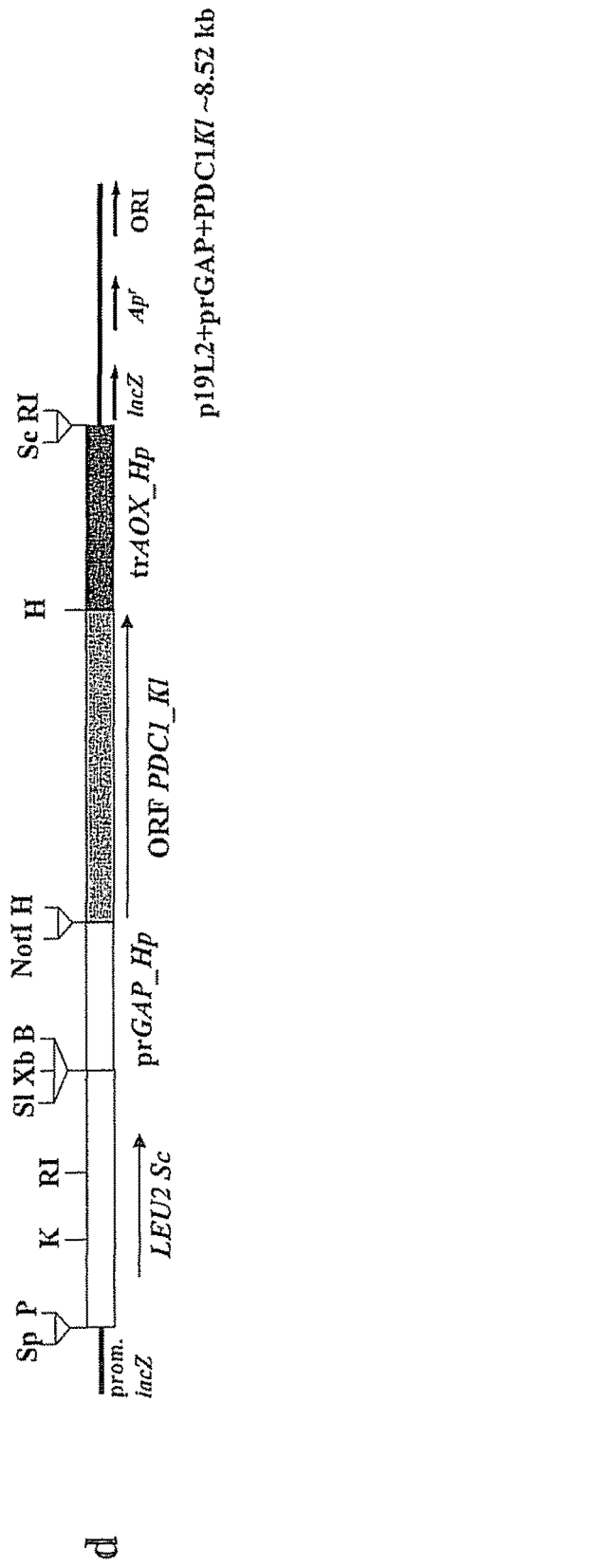
Figure 18:
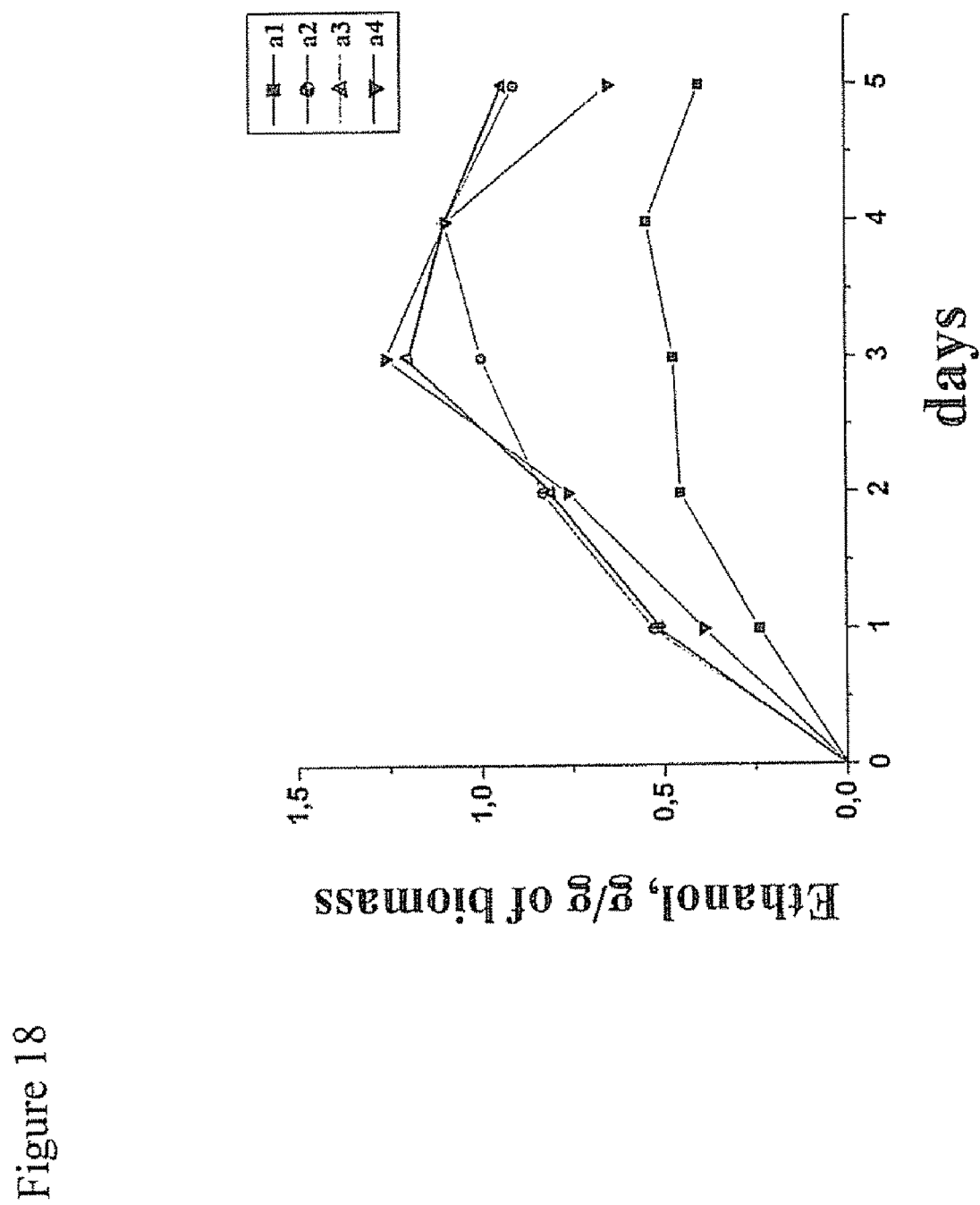
FIG. 18 shows the ethanol productivity during xylose fermentation at 48° C. Strains: a1—2EthOH—, a2—2EthOH-/pGLG61+PDC1Hp-12, a3—2EthOH-/pGLG61+PDC1Hp-13, a4—2EthOH-/ploxZeoloxPDC1Hp-10.
Figure 19:
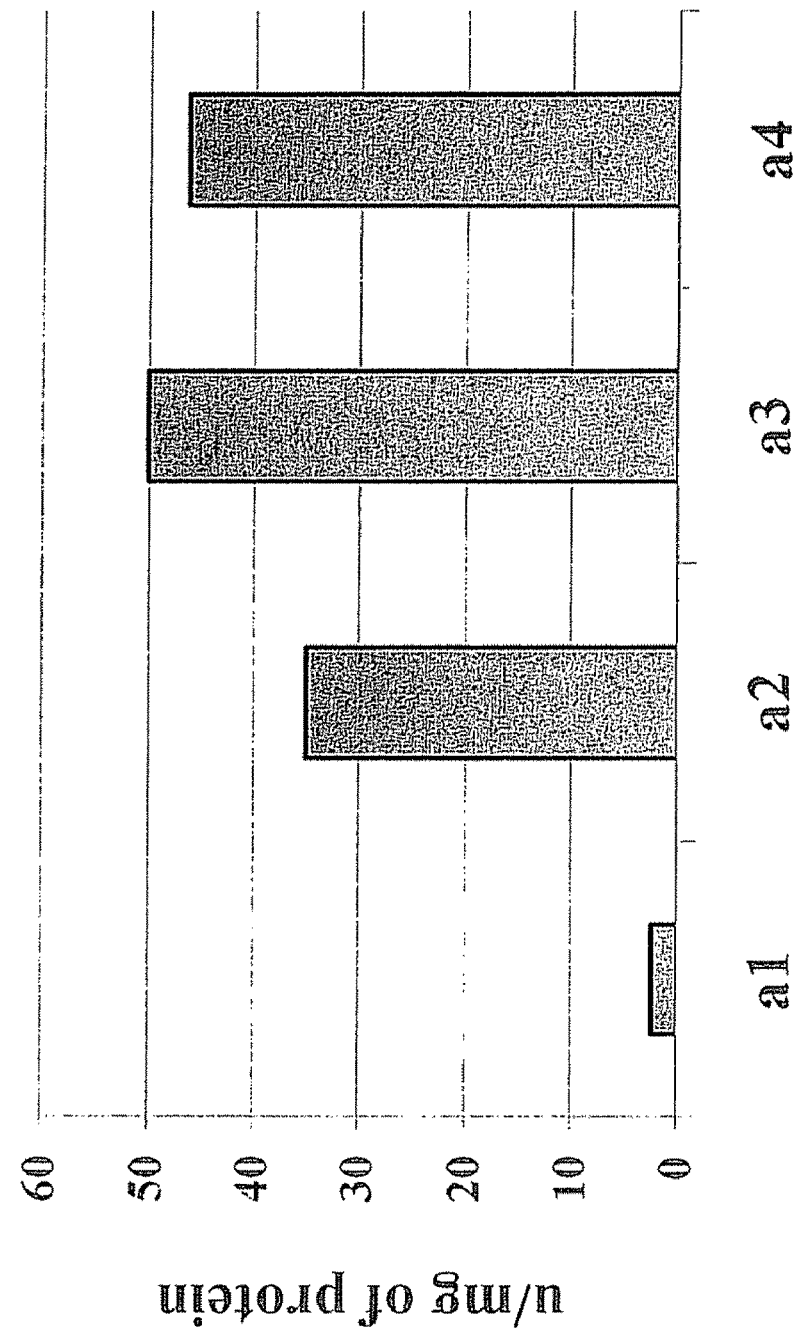
FIG. 19 shows the specific activity of pyruvate decarboxylase of *H. polymorpha* transformants during xylose fermentation at 48° C. Transformants: a1—2EthOH—, a2—2EthOH-/pGLG61+PDC1Hp-12, a3—2EthOH-/pGLG61+PDC1Hp-13, a4—2EthOH-/ploxZeoloxPDC1Hp-10.

2EthOH⁻ transformants carrying PDC1 expression cassette were shown to have improved fermentation of xylose as compared to the recipient strain. In these transformants ethanol synthesis and ethanol productivity during xylose fermentation at 48° C. were approximately 2.3 and 3.0 fold higher, respectively (FIG. 17, FIG. 18). Pyruvate decarboxylase activity was substantially higher: 14.3 fold increase for 2EthOH-/pGLG61+PDC1Hp-12 transformant, 20.3 fold increase for 2EthOH-/pGLG61+PDC1Hp-13 and 18.6 fold increase for 2EthOH-/ploxZeoloxPDC1Hp-10 (FIG. 10).

Figure 20:
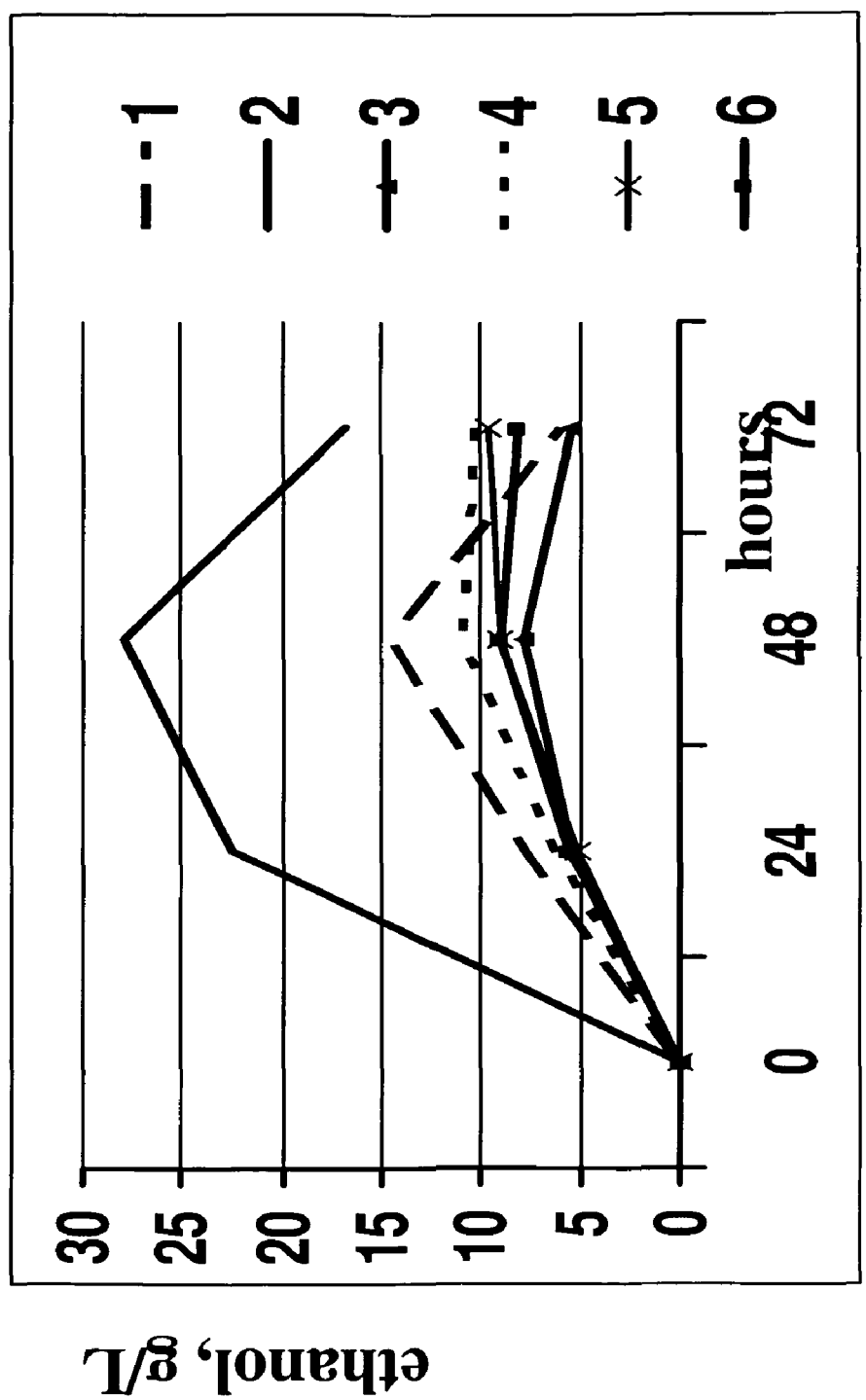
FIG. 20 shows the ethanol productivity during glucose fermentation at 48° C. Strains: 1—3Leu+, 2—PDC1Hp-4, 3—2EthOH—, 4—2EthOH-/ploxZeoloxPDC1Hp-10, 5—2EthOH-/pGLG61+PDC1Hp-12, 6—2EthOH-/pGLG61+PDC1Hp-13.
Figure 21:
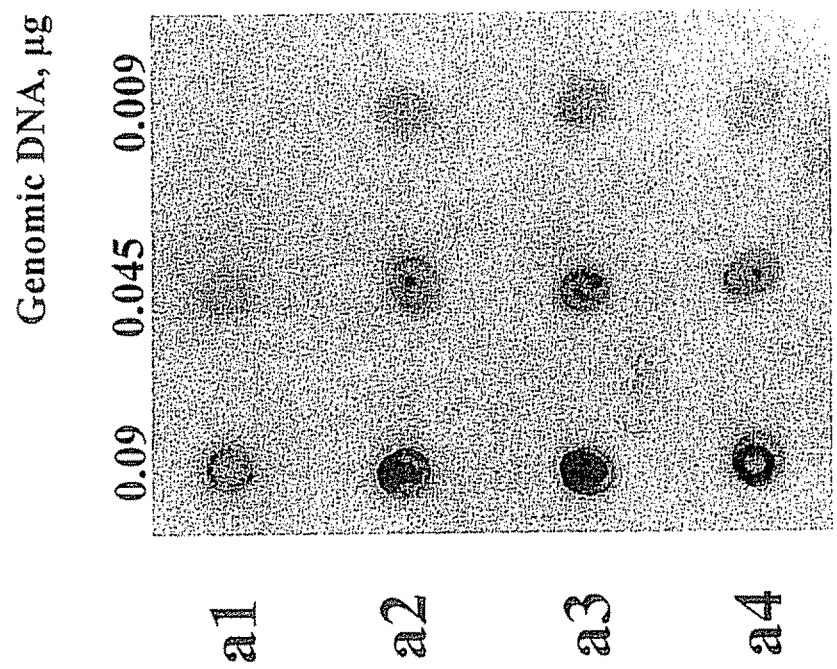
FIG. 21 shows the dot-blot hybridization for PDC1 gene copy estimation. Genomic DNA: a1—2EthOH—, a2—2EthOH-/pGLG61+PDC1Hp-12, a3—2EthOH-/pGLG61+PDC1Hp-13, a4—2EthOH-/ploxZeoloxPDC1Hp-10. ECL-labeled fragment containing *H. polymorpha* PDC1 gene was used as a probe.

Transformants were also characterized by increase in pyruvate decarboxylase activity during cultivation in glucose medium and accumulated elevated amounts of ethanol in glucose medium relative to the 2EthOH⁻ transformant with empty vector (though less than the wild-type transformant) (Table 2, FIG. 20). In the medium with L-arabinose, transformants with elevated pyruvate decarboxylase were characterized by better growth, however no ethanol was accumulated (Table 2).

It was shown with Southern blotting that selected transformants (a2-a4) with improved fermentation of xylose have approximately 7 to 9 copies of PDC1 expression cassettes in the genome of 2EthOH⁻ transformants 2EthOH-/pGLG61+ PDC1Hp-12, 2EthOH-/pGLG61+PDC1Hp-13 and 5 copies in 2EthOH-/ploxZeoloxPDC1Hp-10 as compared to the intensity of signal of the genomic DNA of the recipient strain (a1) which carries just one copy of PDC1 (FIG. 12).

Overexpression of the PDC1 Gene of *K. lactis* in the *H. polymorpha* Wild-Type Strain We decided to confirm that heterologous pyruvate decarboxylase overexpression in *H. polymorpha* could improve the fermentation parameters of this yeast species. For this purpose we cloned the *K. lactis* ORF of PDC1 gene into the expression cassette for *H. polymorpha* and introduced into *H. polymorpha* wild-type strain. The plasmid p19L2+prGAP+ PDC1Kl was linearized and transformed into the NCYC495 leu1-1 strain. The pyruvate decarboxylase activity and ethanol production from xylose were studied in stable Leu+ transformants carrying *K. lactis* PDC1 expression cassette.

Figure 22:
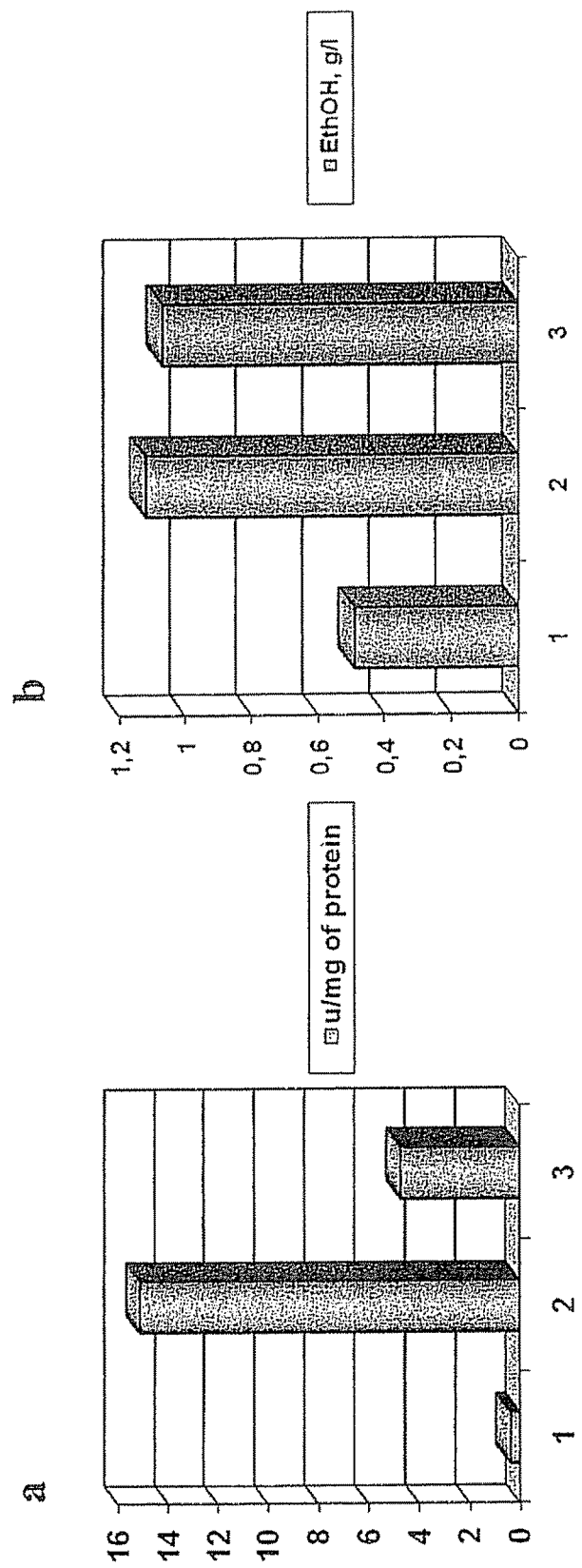
FIG. 22 shows the specific activity of pyruvate decarboxylase and ethanol accumulation of *H. polymorpha* transformants during xylose fermentation at 37° C. Transformants: 1—3Leu+, 2—PDC1Hp-4, 3—PDC1Kl-3. The samples for ethanol concentration estimation and pyruvate decarboxylase assay were taken from the third day of fermentation of xylose (YNB with 8% xylose).

One of the transformant PDC1Kl had 12.8 fold increased pyruvate decarboxylase activity (FIG. 22*a*) and 2.2 fold increased ethanol production (FIG. 22*b*) comparing to the control strain 3Leu+. These results demonstrate that native PDC1 overexpression as well as heterologous one (i.e. *K. lactis*) significantly improve the fermentation parameters of *H. polymorpha*.

The constructed recombinant strains of *H. polymorpha* could be further improved as the xylose transport and first steps of xylose utilizations are limiting for xylose fermentation in this yeast species (Dmytruk O V, Voronovsky A Y, Abbas C A, Dmytruk K V, Ishchuk OP & Sibirny A A (2007) Overexpression of bacterial xylose isomerase and yeast host xylulokinase improves xylose alcoholic fermentation in the thermotolerant yeast *Hansenula polymorpha*. *FEMS Yeast Res* [Epub ahead of print]; Voronovsky et al., 2005).

TABLE 2

Fermentation profiles of *H. polymorpha* strains at 48° C. under restricted aeration (140 rpm) in the YNB media supplied with different carbon sources (12% arabinose, 12% xylose, 12% glucose). The samples were taken for analysis on the second day of fermentation.

| Strains | L-arabinose | | | D-xylose | | | D-glucose | | |
|---|---|---|---|---|---|---|---|---|---|
| | OD, $\lambda 600$ | Ethanol, $g \times L^{-1}$ | Pdc1 activity, u/mg | OD, $\lambda 600$ | Ethanol, $g \times L^{-1}$ | Pdc1 activity, u/mg | OD, $\lambda 600$ | Ethanol, $g \times L^{-1}$ | Pdc1 activity, u/mg |
| 3Leu+ | 10.5 | 0.0 | 0.4 | 8.24 | 0.7 | 0.1 | 12.4 | 14.4 | 0.21 |
| PDC1Hp-4 | 11.2 | 0.0 | 9.2 | 11.0 | 1.2 | 4.1 | 13.0 | 27.9 | 3.2 |
| 2EthOH- | 10.68 | 0.0 | 0.07 | 11.1 | 0.9 | 0.21 | 11.6 | 7.8 | 0.26 |
| 2EthOH-/ploxZeoloxPDC1Hp-10 | 11.12 | 0.0 | 0.88 | 14.1 | 1.6 | 2.2 | 16.2 | 10.8 | 2.9 |
| 2EthOH-/pGLG61 + PDC1Hp-12 | 12.16 | 0.0 | 0.79 | 11.2 | 1.5 | 3.3 | 15.2 | 8.97 | 1.8 |
| 2EthOH-/pGLG61 + PDC1Hp-13 | 12.84 | 0.0 | 1.3 | 13.5 | 1.3 | 1.32 | 15.4 | 9.0 | 1.94 |

Whereas particular embodiments of this invention have been described for purposes of illustration, it will be evident to those persons skilled in the art that numerous variations of the details of the present teaching may be made without departing from the invention as defined in the appended claims. Those patents and publications discussed herein should be viewed as indicative of the level of skill in the art, though no admission is made that any document is a prior art reference. All of the foregoing patents and publications herein are hereby incorporated by reference. To the extent that the incorporated material conflicts with existing definitions, statements, or other disclosure material set forth in this description, the disclosure as explicitly set forth herein supersedes any conflicting material incorporated by reference.

We claim:

1. A process for production of ethanol, comprising:
   (a) isolating from a donor yeast a first polynucleotide comprising a nucleic acid selected from the group consisting of: SEQ ID NO: 3 and SEQ ID NO: 4;
   (b) constructing yeast vectors comprising said polynucleotide;
   (c) transforming a host cell with the vectors obtained in step (b) to obtain a recombinant yeast strain;
   (d) cultivating said recombinant yeast strain in a xylose-containing medium;
   (e) isolating and purifying ethanol formed in said medium.

2. The process of claim 1, including wherein said vectors further comprise a promoter operably associated with said first polynucleotide.

3. The process of claim 2, including wherein said promoter is selected from the group consisting of *Hansenula polymorpha* GAP, PMA1, and TEF1 promoters.

4. The process of claim 2, including wherein said promoter is a *Hansenula polymorpha* glyceraldehyde-3-phosphate dehydrogenase promoter.

5. The process of claim 4, including wherein said promoter has the nucleotide sequence of SEQ ID NO: 5.

6. The process of claim 2, including wherein said vector further comprises a terminator operably associated with said first polynucleotide.

7. The process of claim 6, including wherein said terminator is selected from the group consisting of terminators of the GAP, PMA1, TEF1 and AOX genes.

8. The process of claim 7, including wherein said terminator is a *Hansenula polymorpha* alcohol oxidase terminator.

9. The process of claim 8, including wherein said terminator has the nucleotide sequence of SEQ ID NO:6.

10. An isolated polynucleotide comprising the nucleic acid selected from the group consisting of: SEQ ID NO: 3 and SEQ ID NO: 4.

11. The polynucleotide of claim 10, further comprising a promoter that controls expression of said polypeptide.

12. The polynucleotide of claim 11, wherein said promoter is selected from the group consisting of *Hansenula polymorpha* GAP, PMA1, and TEF1 promoters.

13. The polynucleotide of claim 12, wherein said promoter is a *Hansenula polymorpha* glyceraldehyde-3-phosphate dehydrogenase promoter.

14. The polynucleotide of claim 13, wherein said promoter has the nucleotide sequence of SEQ ID NO: 5.

15. The polynucleotide claim 10, further comprising a terminator.

16. The polynucleotide of claim 15, wherein said terminator is selected from the group consisting of terminators of the GAP, PMA1, TEF1 and AOX genes.

17. The polynucleotide of claim 16, wherein said terminator is a *Hansenula polymorpha* alcohol oxidase terminator.

18. The polynucleotide of claim 17, wherein said terminator has the polynucleotide sequence of SEQ ID NO: 6.

19. An isolated plasmid comprising a polynucleotide of claim 10.

20. An isolated yeast host cell comprising a plasmid of claim 19.

21. The isolated host cell of claim 20, wherein said host cell is a strain of *Hansenula polymorpha*.

22. A process for producing ethanol, comprising:
(a) cultivating an isolated host cell of claim 20 in a xylose-containing medium; and
(b) isolating and purifying ethanol formed in said medium.

* * * * *